US012781171B2

(12) United States Patent
Tian et al.

(10) Patent No.: US 12,781,171 B2
(45) Date of Patent: Nov. 3, 2026

(54) CELL-SENSORY BIOSCAFFOLDS, FABRICATION METHODS AND APPLICATIONS OF SAME

(71) Applicant: BOARD OF TRUSTEES OF THE UNIVERSITY OF ARKANSAS, Little Rock, AR (US)

(72) Inventors: Zheng Ryan Tian, Fayetteville, AR (US); Hanan Alismail, AlRiyadh (SA); Yuchun Du, Fayetteville, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 954 days.

(21) Appl. No.: 17/629,881

(22) PCT Filed: Aug. 7, 2020

(86) PCT No.: PCT/US2020/045340
§ 371 (c)(1),
(2) Date: Jan. 25, 2022

(87) PCT Pub. No.: WO2021/030173
PCT Pub. Date: Feb. 18, 2021

(65) Prior Publication Data

US 2022/0290085 A1 Sep. 15, 2022

Related U.S. Application Data

(60) Provisional application No. 62/884,734, filed on Aug. 9, 2019.

(51) Int. Cl.
*C12M 1/12* (2006.01)
*C12M 1/34* (2006.01)
(Continued)

(52) U.S. Cl.
CPC ............ *C12M 25/12* (2013.01); *C12M 41/46* (2013.01); *G01N 27/3278* (2013.01);
(Continued)

(58) Field of Classification Search
CPC ...... C12M 25/02; C12M 25/12; C12M 41/46; G01N 27/3278; G01N 33/5011; G01N 33/502; G01N 33/5438; G01N 2500/10
See application file for complete search history.

(56) References Cited

U.S. PATENT DOCUMENTS 8,318,297 B2 * 11/2012 Tian ........................ A61L 27/56
428/307.3
2010/0255583 A1 10/2010 Tian

OTHER PUBLICATIONS

Document Details for the reference "A cell-sensory bioscaffold of biocompatible titanate nanofiber", TechConnect Briefs 2018—Advanced Materials, May 2018 (Year: 2018).*

(Continued)

*Primary Examiner* — Matthew D Krcha
*Assistant Examiner* — Austin Q Le
(74) *Attorney, Agent, or Firm* — troutman pepper locke; Tim Tingkang Xia, Esq.

(57) ABSTRACT

A cell sensor and methods of using the cell sensor for differentiating types of cells. The cell sensor includes a sensing member having bioscaffolds comprising nanofibers/nanowires of titanate grown on a titanium sheet. The method includes preparing a cell sensor comprising a sensing member having bioscaffolds comprising nanofibers/nanowires of titanate grown on a titanium sheet; incubating the bioscaffolds with cells in an aqueous solution at an incubation temperature for a period of incubation time, wherein the cells in the aqueous solution include at least one of cancer cells, normal cells, stem cells, and neuron cells; and measuring electrical characteristics of the bioscaffolds to deter- (Continued)

mine the types of the cells based on the measured electrical characteristics.

6 Claims, 27 Drawing Sheets

(51) Int. Cl.
*G01N 27/327* (2006.01)
*G01N 33/50* (2006.01)
*G01N 33/543* (2006.01)
(52) U.S. Cl.
CPC ..... *G01N 33/5011* (2013.01); *G01N 33/5438* (2013.01); *G01N 2500/10* (2013.01)

(56) References Cited

OTHER PUBLICATIONS

Hopkins, Customization of Titanate Nanofiber Bioscaffolds, Biomedical Engineering Undergraduate Honors Theses, 2016, pp. 1-17 (Year: 2016).*
Hanan, A.; Du, Y.; Zhou, J.; Tian, Z. R.; A Cell-Sensory Bioscaffold of Biocompatible Titanate Nanofiber, Proceedings of the 2018 TechConnect World Innovation Conference, Anaheim, LA, (To be published on May 13-16, 2018).
Wang, R. H.; Dong, W. J.; Ruan, C. M.; Kanayeva, D.; Lessiter, K.; Tian, Ryan; Li, Y.B.; TiO2 Nanowire Bundle Microelectrode Based Impedance Immunosensor for Rapid and Sensitive Detection of Listeria monocytogenes, Nano Lett., 9 (12), 4570-4570 (2008).
Dong, W.; Zhang, T.; Epstein, J.; Cooney, L.; Wang, H.; Li, Y.; Jiang, Y-B.; Cogbill, A.; Tian, Z. Ryan; Multifunctional Nanowire Bioscaffolds on Titanium, Chem. Mater, 19, 4454-4459 (2007).
Dong, W. Zhang, T.; McDonald, M.; Padilla, C.; Epstein, J.; Tian, Z. R.; "Biocompatible nanofiber scaffolds on metal for controlled release and cell colonization," Nanomedicine: Nanotech., Biology, & Medicine, 2, 248-252 (2006).
Abraham, J.K.; Dubaka, S.; Varadan, V.K.; Zhou, H.; Zhang, T.; Tian, Z. Ryan; Piezoelectric 3D nanostructures for developing point-of-care biosensors, SPIE Proc, 6528, Apr. 11, 2007.
Asphahani, F. et al. Influence of cell adhesion and spreading on impedance characteristics of cell-based sensors. Biosensors & Bioelectronics 23, 1307-1313, doi:10.1016/j.bios.2007.11.021 (2008).
Asphahani, F. et al. Single-cell bioelectrical impedance platform for monitoring cellular response to drug treatment. Physical Biology 8, doi:10.1088/1478-3975/8/1/015006 (2011).
Blad, B. & Baldetorp, B. Impedance spectra of tumour tissue in comparison with normal tissue; A possible clinical application for electrical impedance tomography. Physiological Measurement 17, A105-A115, doi:10.1088/0967-3334/17/4a/015 (1996).
Cho, Y., Kim, HS., Frazier, AB., Chen, ZG., Shin, DM. & Han, A. Whole-cell impedance analysis for highly and poorly metastatic cancer cells. Journal of Microelectromechanical Systems 18(4), 808-817 (2009).
Cui, Y., An, Y., Jin, TY., Zhang, F. & He, PG. Real-time monitoring of skin wound healing on nano-grooves topography using electric cell-substrate impedance sensing (ECIS). Sensors and Actuators B-Chemical 250, 461-468 (2017).
Dean, D. A., Ramanathan, T., Machado, D. & Sundararajan, R. Electrical impedance spectroscopy study of biological issues. Journal of Electrostatics 66, 165-177, doi:10.1016/j.elstat.2007.11.005 (2008).
Dobrzynska, I., Skrzydlewska, E. & Figaszewski, Z. A. Changes in Electric Properties of Human Breast Cancer Cells. Journal of Membrane Biology 246, 161-166, doi:10.1007/s00232-012-9516-5 (2013).
Foster, K. R. & Schepps, J. L. Dielectric-Properties of Tumor and Normal-Tissues At Radio Through Microwave-Frequencies. Journal of Microwave Power and Electromagnetic Energy 16, 107-119 (1981).
Foster, K. R. & Schwan, H. P. Dielectric-Properties of Tissues and Biological-Materials—A Critical-Review. Critical Reviews in Biomedical Engineering 17, 25-104 (1989).
Ghenim, L. et al. Monitoring impedance changes associated with motility and mitosis of a single cell. Lab on a Chip 10, 2546-2550, doi:10.1039/c004115g (2010).
Giaever, I. & Keese, C. R. Micromotion of Mammalian-Cells Measured Electrically. Proceedings of the National Academy of Sciences of the United States of America 88, 7896-7900, doi:10.1073/pnas.88.17.7896 (1991).
Giaever, I. & Keese, C. R. Monitoring Fibroblast Behavior in Tissue-Culture With an Applied Electric-Field. Proceedings of the National Academy of Sciences of the United States of America-Biological Sciences 81, 3761-3764, doi:10.1073/pnas.81.12.3761 (1984).
Glickman, Y. A. et al. Electrical impedance scanning: a new approach to skin cancer diagnosis. Skin Research and Technology 9, 262-268, doi:10.1034/j.1600-0846.2003.00022.x (2003).
Goller, D. A., Weidema, W. F. & Davies, R. J. Transmural Electrical Potential Difference as an Early Marker in Colon Cancer. Archives of Surgery 121, 345-350 (1986).
Han, A., Yang, L. & Frazier, A. B. Quantification of the heterogeneity in breast cancer cell lines using whole-cell mpedance spectroscopy. Clinical Cancer Research 13, 139-143, doi:10.1158/1078-0432.ccr-06-1346 (2007).
Jossinet, J. The impedivity of freshly excised human breast tissue. Physiological Measurement 19, 61-75, doi:10.1088/0967-3334/19/1/006 (1998).
Jossinet, J. Variability of impedivity in normal and pathological breast tissue. Medical & Biological Engineering & Computing 34, 346-350, doi:10.1007/bf02520002 (1996).
Mitra, P., Keese, C. R. & Giaever, I. Electric measurements can be used to monitor the attachment and spreading of cells in tissue-culture. Biotechniques 11, 504-& (1991).
Morimoto, T. et al. Measurement of the Electrical Bioimpedance of Breast-Tumors. European Surgical Research 22, 86-92, doi:10.1159/000129087 (1990).
O'Rourke, A. P. et al. Dielectric properties of human normal, malignant and cirrhotic liver tissue: in vivo and ex vivo measurements from 0.5 to 20 GHz using a precision open-ended coaxial probe. Physics in Medicine and Biology 52, 4707-4719, doi:10.1088/0031-9155/52/15/022 (2007).
Pethig, R. Dielectric properties of body tissues. Clinical physics and physiological measurement: an official journal of the Hospital Physicists' Association, Deutsche Gesellschaft fur Medizinische Physik and the European Federation of Organisations for Medical Physics 8 Suppl A, 5-12, doi:10.1088/0143-0815/8/4a/002 (1987).
Pethig, R. Dielectric-Properties of Biological-Materials—Biophysical and Medical Applications. IEEE Transactions on Electrical Insulation 19, 453-474, doi:10.1109/tei.1984.298769 (1984).
Polk, C. & Postow, E. CRC handbook of biological effects of electromagnetic fields. CRC handbook of biological effects of electromagnetic fields., i-xiii, 1-503 (1986).
Qiao, G. F. et al. Bioimpedance Analysis for the Characterization of Breast Cancer Cells in Suspension. IEEE Transactions on Biomedical Engineering 59, 2321-2329, doi:10.1109/tbme.2012.2202904 (2012).
Richard J Davies. Underlying mechanisms involved in surface electrical potential measurements for the diagnosis of breast cancer: an electrophysiological approach to cancer diagnosis, In Electropotentials in the Clinical Assessment of Breast Neoplasia. pp. 3-17 (1996).
Schwan, H. P. Electrical properties of tissue and cell suspensions. Advances in biological and medical physics 5, 147-209 (1957).
Srinivasaraghavan, V., Strobl, J. & Agah, M. Bioimpedance rise in response to histone deacetylase inhibitor is a marker of mammary cancer cells within a mixed culture of normal breast cells. Lab on a Chip 12, 5168-5179, doi:10.1039/c2c40778g (2012).
Vistejnova, L. et al. The comparison of impedance-based method of cell proliferation monitoring with commonly used metabolic-based techniques. Neuroendocrinology Letters 30, 121-127 (2009).
Wanekaya, A. K., Chen, W., Myung, N. V. & Mulchandani, A. Nanowire-based electrochemical biosensors. Electroanalysis 18, 533-550, doi:10.1002/elan.200503449 (2006).

(56) References Cited

OTHER PUBLICATIONS

Wegener, J., Keese, C. R. & Giaever, I. Electric cell-substrate impedance sensing (ECIS) as a noninvasive means to monitor the kinetics of cell spreading to artificial surfaces. Experimental Cell Research 259, 158-166, doi:10.1006/excr.2000.4919 (2000).

Xiao, C. & Luong, J. H. T. On-line monitoring of cell growth and cytotoxicity using electric cell-substrate impedance sensing (ECIS). Biotechnology Progress 19, 1000-1005, doi:10.1021/bp025733x (2003).

Yang, L. J., Arias, L. R., Lane, T. S., Yancey, M. D. & Mamouni, J. Real-time electrical impedance-based measurement to distinguish oral cancer cells and non-cancer oral epithelial cells. Analytical and Bioanalytical Chemistry 399, 1823-1833, doi:10.1007/s00216-010-4584-9 (2011).

Korean Intellectual Property Office (ISR/KR), "International Search Report for PCT/US2020/045340", Korea, Nov. 19, 2020.

Alismail, Hanan et al., 'A cell-sensory bioscaffold of biocompatible titanate nanofiber', TechConnect Briefs, 2018, ISBN 978-0-9988782-4-9, pp. 42-45.

Alismail, Hanan et al., 'Titanate TiO2 nanowire bio-scaffold as a novel sensor for cancer cell differentiation', In: 23rd International Conference on Nanomaterials science & Nanoengineering & Technology & International Conference and Exhibition on Pharmaceutical Nanotechnology and Nanomedicine. Journal of Nanomedicine & Nanotechnology, 2018, vol. 9, ISSN: 2157-7439, p. 87.

Hu, Anming et al., 'Hydrothermal growth of free standing TiO2 nanowire membranes for photocatalytic degradation of pharmaceuticals', Journal of Hazardous Materials, 2011, vol. 189, pp. 278-285.

Yang, Liju et al., 'Real-time electrical impedance-based measurement to distinguish oral cancer cells and non-cancer oral epithelial cells', Analytical and Bioanalytical Chemistry, 2011, vol. 399, pp. 1823-1833.

* cited by examiner

CELL-SENSORY BIOSCAFFOLDS, FABRICATION METHODS AND APPLICATIONS OF SAME

CROSS-REFERENCE TO RELATED PATENT APPLICATION

This PCT application claims priority to and the benefit of U.S. Provisional Patent Application Ser. No. 62/884,734, filed Aug. 9, 2019, which is incorporated herein by reference in its entirety.

FIELD OF THE INVENTION

The invention relates generally to biosensors, and more particularly, to cell-sensory bioscaffolds, fabrication methods and applications of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Breast cancer patients have been increasing in number causing a high health threat worldwide. According to the American Cancer Society, breast cancer is the most common non-cutaneous cancer in women in the US. Breast cancer has a 14% mortality rate among women and the rate is the second highest among all types of cancer. Current diagnostic technology utilizes a combination of radiological, surgical, and pathologic assessments. Diagnosis of breast cancer is routinely done by mammogram, but it cannot distinguish between benign and malignant lesions. Mammogram also fails to detect 10% to 25% of breast cancers, because tumor detection is difficult in dense breast tissue. A biopsy is also needed to confirm or role out cancer, and it requires significant sample preparation using bench top protocols. PCR and flow cytometry also have been used for detecting circulating cancer cells in the blood and may predict the survival rate. However, both techniques require using specific tagging system and identifying particular markers, which may not be expressed in some cancer subpopulations. Also, they lead to cell destruction and loss of cell viability. Therefore, there is a high demand to solve this issue by developing further advanced technology to improve sensitivity and selectivity in breast cancer detection. The technology should also be simple, efficient, and inexpensive.

To date, most electrochemical methods for cell-sensing need to put cells on a sensory surface, which is the environment far from that of the bioscaffold and lets the cells experience some unnecessary physical and chemical stress. Other cell-sensing methods should destroy the cell to analyze the DNA, which is uneasy to lay-users and not good for studying cell behavior under the different chemical/physical stresses. Thus in clinic labs of oncological pathology, for instance, a low-cost sensor that can simply distinguish the noncancerous, deadly and indolent cancerous cells from the same site of autopsy for making the pathological tests easier, faster, more accurate, and less costly has been long-overdue.

Recently, nanowire material has attracted attention as an excellent material to be used in biosensing technology. This is due to its unique properties of being semiconducting with high sensitivity to detect a single molecule. Titanium oxide ($TiO_2$) based semiconductor nanowires can be grown on the top of titanium metal and, in turn, it can be used as an electrode to sense cancer cells. These $TiO_2$ nanowires have a band gap between 1.8 and 4.1 eV. This range reflect a semiconductor property making them unique from other nanowires by having the best sensitivity ranges. Besides, $TiO_2$ nanowires are easily fabricated, highly biocompatible and chemically more stable. Thus, $TiO_2$ nanowires are ideal for sensing purposes. However, to the best of our knowledge, little has been reported in literature so far on turning a bioscaffold into an electrochemical sensor, because often bioscaffolds are electrochemically inactive. Thus, in general, turning a bioscaffold into an electrochemical biosensor seems nearly impossible to most developers of new diagnostic tools including biosensors.

Therefore, a heretofore unaddressed need exists in the art to address the aforementioned deficiencies and inadequacies.

SUMMARY OF THE INVENTION

One of the objectives of the invention is to provide bioscaffolds of $TiO_2$ nanowires for sensing electrochemical properties of cells and applying them in developing a prognostic tool for diagnostic technology. This novel method can also be used in various important applications in cancer screening and monitoring, which are doable in vitro at ultra-low-cost and in real-time.

In one aspect, the invention relates to bioscaffolds comprising nanofibers/nanowires of titanate grown on a titanium sheet.

In one embodiment, the nanofibers/nanowires of titanate are grown under a hydrothermal process.

In one embodiment, the nanofibers/nanowires of titanate are entangled atop and self-assembled into scaffolds with concave nests on the titanium sheet.

In another aspect, the invention relates to a cell sensor comprising a sensing member having bioscaffolds comprising nanofibers/nanowires of titanate grown on a titanium sheet, wherein in operation, the bioscaffolds are incubated with cells in an aqueous solution at an incubation temperature for a period of incubation time, wherein the cells in the aqueous solution include at least one of cancer cells, normal cells, stem cells, and neuron cells, and different types of cells produce differences in impedance change within certain frequencies on the bio scaffolds.

In one embodiment, the cell sensor further comprises an electrode coupled to the sensing member.

In one embodiment, the nanofibers/nanowires of titanate are grown under a hydrothermal process.

In one embodiment, the nanofibers/nanowires of titanate are entangled atop and self-assembled into scaffolds with concave nests on the sensing member.

In one embodiment, different ratios of the cancer cells in the normal cells shifted the mixture's electrochemical signals quantitatively and reproducibly.

In one embodiment, the cancer cells alter the surface charge-density of the bio scaffolds more than that of the normal cells while binding to the surface of nanofibers/nanowires of the bioscaffolds.

In one aspect, the invention relates to a method for fabricating a cell sensor. The method includes providing a titanium sheet; sonicating the titanium sheet in acetone at room temperature for a first period of time, and then rinsing the sonicated titanium sheet; placing the rinsed titanium sheet in a NaOH solution to form a mixture thereof in a vessel and sealing the vessel; hydrothermally treating the mixture of the titanium sheet and the NaOH solution sealed in the vessel in a heater at a predetermined temperature for a second period of time, thereby forming a sensing member having titanate nanowires-entangled scaffolds grown on the titanium sheet, and then cooling the vessel for a third period of time; rinsing the sensing member until pH of the surface of the sensing member reaches about 7, and drying the rinsed sensing member in air; and attaching an electrode onto an edge of the dried sensing member so as to form a cell sensor having a cell sensing area.

In one embodiment, the first period of time is in a range of about 12 min to about 18 min.

In one embodiment, the step of rinsing the sonicated titanium sheet is performed with distilled de-ionized (DDI) water.

In one embodiment, the predetermined temperature is in a range of about 128° C. to about 300° C.

In one embodiment, the second period of time is in a range of about 3.2 hrs to about 30 hrs and the third period of time is in a range of about 3.2 hrs to about 28.8 hrs.

In one embodiment, the step of cooling the vessel is performed in air outside of the heater.

In one embodiment, the step of rinsing the sensing member is performed with DDI water.

In one embodiment, the step of attaching the electrode is performed by epoxy-gluing.

In one embodiment, the method further comprises, prior to attaching the electrode, scratching an edge surface of the sensing member to expose the titanium on which the electrode is attached.

In another aspect, the invention relates to a method for differentiating types of cells comprising providing a cell sensor comprising a sensing member having bioscaffolds comprising nanofibers/nanowires of titanate grown on a titanium sheet; incubating the bioscaffolds with cells in an aqueous solution at an incubation temperature for a period of incubation time, wherein the cells in the aqueous solution include at least one of cancer cells, normal cells, stem cells, and neuron cells; and measuring electrical characteristics of the bioscaffolds to determine the types of the cells based on the measured electrical characteristics.

In one embodiment, the measured electrical characteristics comprises impedance.

In one embodiment, the electrical characteristics is dependent on at least one of the cells, the incubation temperature, the period of incubation time, and pH and components of the aqueous solution.

In one embodiment, different types of cells produce differences in impedance change within certain frequencies on the bioscaffolds.

In one embodiment, the cancer cells alter the surface charge-density of the bio scaffolds more than that of the normal cells while binding to the surface of nanofibers/nanowires of the bioscaffolds.

In one embodiment, the aqueous solution contains phosphate buffer saline (PBS).

In one embodiment, the PBS is prepared by charging DDI water and stirring charged DDI water with a magnetic stirrer while adding chemicals in the order of sodium chloride (NaCl), potassium chloride (KCl), sodium phosphate dibasic ($Na_2HPO_4$), and potassium phosphate dibasic ($KH_2PO_4$).

In one embodiment, the pH of the aqueous solution is adjusted to in a range of about 6-8 by titrating with a hydrochloric acid (HCL) solution.

In one embodiment, the aqueous solution contains about 100-1,000,000 cells/ml, preferably, about 1,000-10,000 cells/ml.

In one embodiment, the incubation temperature is in a range of room temperature to about 37° C., and the period of incubation time is in a range of about 5-35 minutes.

In one embodiment, a mixing ratio of the cancer cells to the normal cells in the aqueous solution ranges from about 1:1000 to about 1:5.

In one embodiment, shift of impedance signals correlates linearly with the mixing ratio.

In one embodiment, the aqueous solution further contains at least one of glucose and chemotherapeutic drug.

In one embodiment, the chemotherapeutic drug comprises doxorubicin (DOX).

In one embodiment, the cells includes one or more of MCF10A, MCF7 and MDA-MB231 and HCT116, wherein MCF10A is a normal human epithelial cell line, MCF7 is a human non-invasive epithelial breast cancer cell line, MDA-MB231 is a human invasive epithelial breast cancer cell line, and HCT116 is a colon cancer cell line.

In one embodiment, the step of measuring the electrical characteristics of the bio scaffolds comprises placing a reference electrode in the aqueous solution; applying an AC signal having a frequency to the reference electrode; and measuring the electrical characteristics of the bioscaffolds of the cell sensor accordingly.

In one embodiment, the frequency is changed starting from about 30 kHz to about 1 MHz.

In one embodiment, the method further comprises measuring the electrical characteristics of the bioscaffolds of the cell sensor in absence of the cells in the aqueous solution; and comparing the measured electrical characteristics of the bioscaffolds of the cell sensor incubated the with the cells in the aqueous solution to the electrical characteristics of the bio scaffolds of the cell sensor in absence of the cells in the aqueous solution, so as to differentiate the types of cells.

In one embodiment, the method further comprises wiredly or wirelessly transmitting the measured electrical characteristics to a computer or a smart device for further processing and/or display.

In yet another aspect, the invention relates to a method for selectively detecting different metabolic wastes of different live cells from digesting different nutrients or from reacting with different drugs over the time. The method comprises placing a cell sensor comprising bioscaffolds in an aqueous solution at a temperature for a period of time, wherein the aqueous solution contains live cells, and nutrients and/or drugs; and measuring electrical characteristics of the bioscaffolds to determine different metabolic wastes of different live cells from digesting different nutrients or from reacting with different drugs based on the measured electrical characteristics.

In one embodiment, the measured electrical characteristics comprises impedance.

In one embodiment, the aqueous solution contains phosphate buffer saline (PBS).

In one embodiment, the electrical characteristics is dependent on at least one of the cells, the temperature, the period of time, and pH and components of the aqueous solution.

In one embodiment, the nutrients comprise glucose.

In one embodiment, the drugs comprises doxorubicin (DOX).

In one aspect, the invention relates to a method for determining efficacy of drug-based reaction related to cell behavior, comprising measuring electrical characteristics of bio scaffolds of a cell sensor placed in an aqueous solution containing live cells before and after the live cells are administrated with a drug, respectively; and comparing the measured electrical characteristics before and after the live cells are administrated with the drug to determine the efficacy of the drug.

In one embodiment, the measured electrical characteristics comprises impedance.

In another aspect, the invention relates to a method for quantifying and characterizing bio-objects, comprising providing a cell sensor comprising bioscaffolds; incubating the bioscaffolds with bio-objects in an aqueous solution at a temperature for a period of time; and measuring electrical characteristics of bio scaffolds to quantify and characterize bio-objects based on the measured electrical characteristics.

In one embodiment, the measured electrical characteristics comprises impedance.

In one embodiment, different types of bio-objects produce differences in impedance change within certain frequencies on the bioscaffolds.

In one embodiment, the cancer cells alter the surface charge-density of the bio scaffolds more than that of the normal cells while binding to the surface of the bioscaffolds.

In one embodiment, the bioscaffolds comprise titanate nanofibers/nanowires grown on a titanium sheet.

In one embodiment, the bio-objects comprise cells, biological tissues, or bacteria.

In one embodiment, the aqueous solution contains phosphate buffer saline (PBS).

In one embodiment, the pH of the aqueous solution is adjustable.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

DETAILED DESCRIPTION OF THE INVENTION

Figure 1:
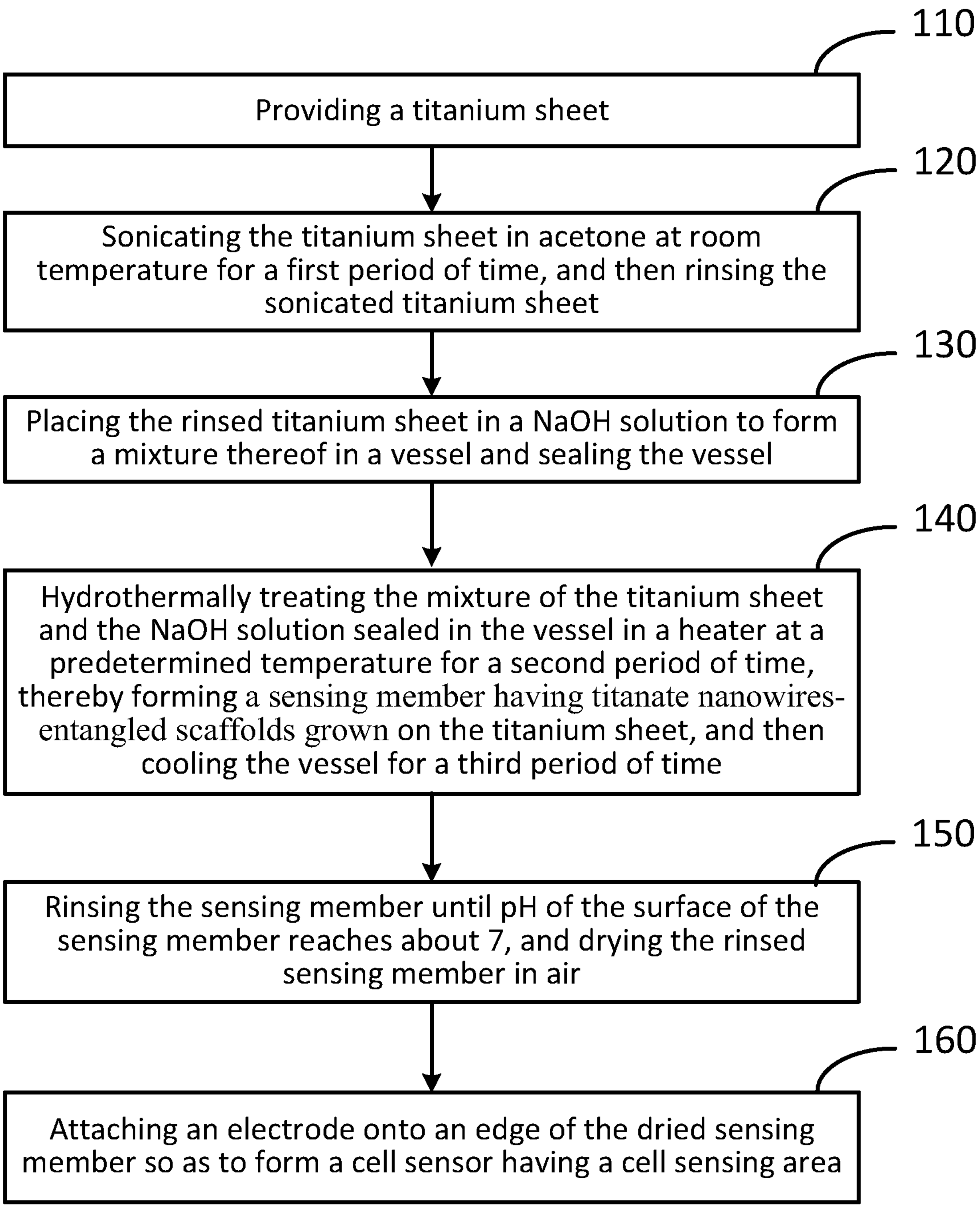
FIG. 1 shows a schematic illustration of hydrothermal synthesis process for $TiO_2$ based nanowires, according to embodiments of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of “a”, “an”, and “the” includes plural reference unless the context clearly dictates otherwise. Thus, for example, reference to “a cell” includes a plurality of such cells and equivalents thereof known to those skilled in the art. As well, the terms “a” (or “an”), “one or more” and “at least one” can be used interchangeably herein. It is also to be noted that the terms “comprising”, “including”, and “having” can be used interchangeably.

It will be understood that when an element is referred to as being “on”, “attached” to, “connected” to, “coupled” with, “contacting”, etc., another element, it can be directly on, attached to, connected to, coupled with or contacting the other element or intervening elements may also be present. In contrast, when an element is referred to as being, for example, “directly on”, “directly attached” to, “directly connected” to, “directly coupled” with or “directly contacting” another element, there are no intervening elements present. It will also be appreciated by those of skill in the art that references to a structure or feature that is disposed “adjacent” another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as “lower” or “bottom” and “upper” or “top,” may be used herein to describe one element’s relationship to another element as illustrated in the figures. It will be understood that relative terms are intended to encompass different orientations of the device in addition to the orientation depicted in the figures. For example, if the device in one of the figures is turned over, elements described as being on the “lower” side of other elements would then be oriented on “upper” sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising", or "includes" and/or "including", or "has" and/or "having", or "carry" and/or "carrying", or "contain" and/or "containing", or "involve" and/or "involving", "characterized by", and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in the disclosure, the phrase "at least one of A, B, and C" should be construed to mean a logical (A or B or C), using a non-exclusive logical OR. As used herein, the term "and/or" includes any and all combinations of one or more of the associated listed items.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In the field of cancer pathology, there is an increasing and long-unmet need to develop a new technology for low-cost, rapid, sensitive, selective, label-free (i.e., direct), simple and reliable screening, diagnosis, and monitoring of live cancer and normal cells in same shape and size from the same anatomic region.

For decades, nanowires have attracted wide attentions on the development of new biosensors. Methodologically, the electrochemical, e.g., the impedance and cyclic voltammetry (CV), sensing of either bacteria (e.g., *Salmonella* and *Listeria*) or biomolecules (e.g., cytochrome C) have been realized directly on the titanate nanowires, thanks to their widely varying bandgap between 1.8 eV and 4.1 eV. Further, the titanate nanowires have been grown directly on the top of the titanium metal to form the macroporous bioscaffolds that can support the controllable elution of drug, and the proliferation of mesenchymal stem-cells and neurons with the right mechanical interlocking besides adhesion of tissues which is what the smooth-surface bioimplants cannot do. Moreover, the one-step synthesis of the nanowire-bioscaffold is easy, simple, low-cost, and scalable for mass-production. Logically, these properties of the titanate-nanowires should be integrated together for developing rationally the first-ever and long-overdue bioscaffold-based cell sensor that can electrochemically differentiate the live and natural cancerous and noncancerous cells in/on the bioscaffold. However, to the best of inventors' knowledge, little has been reported in literature so far on turning a bioscaffold into an electrochemical sensor, because often bioscaffolds are electrochemically inactive. Thus, in general, turning a bioscaffold into an electrochemical biosensor seems nearly impossible to most developers of new diagnostic tools including biosensors.

The invention in one aspect provides bioscaffolds comprising nanofibers/nanowires of titanate grown on a titanium sheet. The nanofibers/nanowires of titanate are entangled atop and self-assembled into scaffolds with concave nests on the titanium sheet.

In some embodiments, the nanofibers/nanowires of titanate are grown under a hydrothermal process.

In another aspect, the invention relates to a cell sensor comprising a sensing member having bioscaffolds comprising nanofibers/nanowires of titanate grown on a titanium sheet. In operation, the bioscaffolds are incubated with cells in an aqueous solution at an incubation temperature for a period of incubation time, wherein the cells in the aqueous solution include at least one of cancer cells, normal cells, stem cells, and neuron cells, and different types of cells produce differences in impedance change within certain frequencies on the bioscaffolds. The nanofibers/nanowires of titanate are entangled atop and self-assembled into scaffolds with concave nests on the sensing member.

In some embodiments, the cell sensor further comprises an electrode coupled to the sensing member.

In some embodiments, the nanofibers/nanowires of titanate are grown under a hydrothermal process.

In some embodiments, different ratios of the cancer cells in the normal cells shifted the mixture's electrochemical signals quantitatively and reproducibly.

In some embodiments, the cancer cells alter the surface charge-density of the bio scaffolds more than that of the normal cells while binding to the surface of nanofibers/nanowires of the bioscaffolds.

In addition, the invention also discloses to a method for fabricating a cell sensor. Referring to FIG. 1, one embodiment of the fabricating method is shown, which includes the following steps.

At step 110, a titanium sheet is prepared.

At step 120, the titanium sheet is sonicated in acetone at room temperature for a first period of time, and then the sonicated titanium sheet is rinsed. In some embodiments, the first period of time is in a range of about 12 min to about 18 min. In some embodiments, the step of rinsing the sonicated titanium sheet is performed with distilled de-ionized (DDI) water.

At step 130, the rinsed titanium sheet is placed in a NaOH solution to form a mixture thereof in a vessel and then the vessel is sealed.

At step 140, the mixture of the titanium sheet and the NaOH solution sealed in the vessel is hydrothermally treated in a heater (e.g., an oven) at a predetermined temperature for a second period of time, thereby forming a sensing member having titanate nanowires-entangled scaffolds grown on the titanium sheet, and then the vessel is cooled for a third period of time. In some embodiments, the predetermined temperature is in a range of about 128° C. to about 300° C. In some embodiments, the second period of time is in a range of about 3.2 hrs to about 30 hrs and the third period of time is in a range of about 3.2 hrs to about 28.8 hrs. In some embodiments, the step of cooling the vessel is performed in air outside of the heater.

At step 150, the sensing member is rinsed until pH of the surface of the sensing member reaches about 7, and the rinsed sensing member is dried in air. In some embodiments, the step of rinsing the sensing member is performed with DDI water.

At step 160, an electrode is attached onto an edge of the dried sensing member so as to form a cell sensor having a cell sensing area. In some embodiments, the step of attaching the electrode is performed by epoxy-gluing.

In some embodiments, the method may further comprise, prior to attaching the electrode, scratching an edge surface of the sensing member to expose the titanium on which the electrode is attached.

It should be appreciated that although the method shown in FIG. 1 is for fabricating a single cell sensor, the method can also be utilized to fabricate a batch of cell sensors. For example, practically, a plurality of titanium sheets can be disposed in acetone, and then steps 120-160 can be applied to fabricate a plurality of cell sensors, each including a titanium sheet.

Another aspect of the invention provides a method for differentiating types of cells.

The method in one embodiment comprises providing a cell sensor comprising a sensing member having bioscaffolds comprising nanofibers/nanowires of titanate grown on a titanium sheet; incubating the bio scaffolds with cells in an aqueous solution at an incubation temperature for a period of incubation time, wherein the cells in the aqueous solution include at least one of cancer cells, normal cells, stem cells, and neuron cells; and measuring electrical characteristics of the bioscaffolds to determine the types of the cells based on the measured electrical characteristics.

In some embodiments, the measured electrical characteristics comprises impedance.

In some embodiments, the electrical characteristics is dependent on at least one of the cells, the incubation temperature, the period of incubation time, and pH and components of the aqueous solution.

In some embodiments, different types of cells produce differences in impedance change within certain frequencies on the bioscaffolds.

In some embodiments, the cancer cells alter the surface charge-density of the bio scaffolds more than that of the normal cells while binding to the surface of nanofibers/nanowires of the bioscaffolds.

In some embodiments, the aqueous solution contains phosphate buffer saline (PBS).

In some embodiments, the PBS is prepared by charging DDI water and stirring charged DDI water with a magnetic stirrer while adding chemicals in the order of sodium chloride (NaCl), potassium chloride (KCl), sodium phosphate dibasic ($Na_2HPO_4$), and potassium phosphate dibasic ($KH_2PO_4$).

In some embodiments, the pH of the aqueous solution is adjusted to in a range of about 6-8 by titrating with a hydrochloric acid (HCL) solution.

In some embodiments, the aqueous solution contains about 100-1,000,000 cells/ml, preferably, about 1,000-10,000 cells/ml.

In some embodiments, the incubation temperature is in a range of room temperature to about 37° C., and the period of incubation time is in a range of about 5-35 minutes.

In some embodiments, a mixing ratio of the cancer cells to the normal cells in the aqueous solution ranges from about 1:1000 to about 1:5.

In some embodiments, shift of impedance signals correlates linearly with the mixing ratio.

In some embodiments, the aqueous solution further contains at least one of glucose and chemotherapeutic drug.

In some embodiments, the chemotherapeutic drug comprises doxorubicin (DOX).

In some embodiments, the cells includes one or more of MCF10A, MCF7 and MDA-MB231 and HCT116, wherein MCF10A is a normal human epithelial cell line, MCF7 is a human non-invasive epithelial breast cancer cell line, MDA-MB231 is a human invasive epithelial breast cancer cell line, and HCT116 is a colon cancer cell line.

In some embodiments, the step of measuring the electrical characteristics of the bioscaffolds comprises placing a reference electrode in the aqueous solution; applying an AC signal having a frequency to the reference electrode; and measuring the electrical characteristics of the bioscaffolds of the cell sensor accordingly.

In some embodiments, the frequency is changed starting from about 30 kHz to about 1 MHz.

In some embodiments, the method further comprises measuring the electrical characteristics of the bioscaffolds of the cell sensor in absence of the cells in the aqueous solution; and comparing the measured electrical characteristics of the bioscaffolds of the cell sensor incubated the with the cells in the aqueous solution to the electrical characteristics of the bioscaffolds of the cell sensor in absence of the cells in the aqueous solution, so as to differentiate the types of cells.

In some embodiments, the method further comprises wiredly or wirelessly transmitting the measured electrical characteristics to a computer or a smart device for further processing and/or display.

Yet another aspect of the invention also provides a method for selectively detecting different metabolic wastes of different live cells from digesting different nutrients or from reacting with different drugs over the time. The method comprises placing a cell sensor comprising bioscaffolds in an aqueous solution at a temperature for a period of time, wherein the aqueous solution contains live cells, and nutrients and/or drugs; and measuring electrical characteristics of the bioscaffolds to determine different metabolic wastes of different live cells from digesting different nutrients or from reacting with different drugs based on the measured electrical characteristics.

In some embodiments, the measured electrical characteristics comprises impedance.

In some embodiments, the aqueous solution contains phosphate buffer saline.

In some embodiments, the electrical characteristics is dependent on at least one of the cells, the temperature, the period of time, and pH and components of the aqueous solution.

In some embodiments, the nutrients comprise glucose.

In some embodiments, the drugs comprises doxorubicin.

In one aspect, the invention relates to a method for determining efficacy of drug-based reaction related to cell behavior, comprising measuring electrical characteristics of bio scaffolds of a cell sensor placed in an aqueous solution containing live cells before and after the live cells are administrated with a drug, respectively; and comparing the measured electrical characteristics before and after the live cells are administrated with the drug to determine the efficacy of the drug.

In some embodiments, the measured electrical characteristics comprises impedance.

In another aspect, the invention relates to a method for quantifying and characterizing bio-objects, comprising providing a cell sensor comprising bioscaffolds; incubating the bioscaffolds with bio-objects in an aqueous solution at a temperature for a period of time; and measuring electrical characteristics of bioscaffolds to quantify and characterize bio-objects based on the measured electrical characteristics.

In some embodiments, the measured electrical characteristics comprises impedance.

In some embodiments, different types of bio-objects produce differences in impedance change within certain frequencies on the bioscaffolds.

In some embodiments, the cancer cells alter the surface charge-density of the bio scaffolds more than that of the normal cells while binding to the surface of the bioscaffolds.

In some embodiments, the bioscaffolds comprise titanate nanofibers/nanowires grown on a titanium sheet.

In some embodiments, the bio-objects comprise cells, biological tissues, or bacteria.

In some embodiments, the aqueous solution contains phosphate buffer saline.

In some embodiments, the pH of the aqueous solution is adjustable.

According to the invention, for the first time on using an impedance signal, the breast cancer and normal cells have been thus screened, diagnosed and monitored on a smart bioscaffold of entangled nanowires of bioceramics titanate grown directly on the surface of implantable Ti-metal and characterized by means of X-ray diffraction (XRD), scanning electron microscope (SEM) couple with the energy dispersive X-ray analysis (SEM-EDX), etc., following a technology patented by Tian et al. (U.S. Pat. No. 8,318,297B2 and EP2101687A2), which are incorporated herein by reference in their entireties. In certain embodiments, in the aqueous solution of PBS, human breast benign (MCF7) and aggressive (MDA-MB231) cancer cells, normal (MCF10A) cells, and colon cancer cells (HCT116) showed characteristic impedance spectra highly different than that of the blank sensor, i.e., no cells on the bioscaffold surface. For two sets of mixtures each containing the normal and cancer cells over a wide range of mixing ratios, the shift of impedance signals has been linearly correlated with the mixing ratios which supports the biosensor's selectivity and reliability. After being treated with pure glucose and/or chemotherapeutic drug, e.g., DOX, with one after the other, the breast cancer cells showed different impedance signals corresponding to their difference in glucose metabolisms (i.e., Warburg effect) and resistances to the DOX, thereby fingerprinting the cells easily. Based on the nano structure chemistry, impedance equivalent circuitry and cancer cell biology, it is the different cells surface binding on the nanowires, and different cancer cells metabolic wastes from the different treatments on the nanowires that changed the charge density on the scaffolding nanowire surface and in turn changed the impedance signals. The method is expandable to quantifying and characterizing live cells and even biological tissues of different types in general.

In certain embodiments, electrochemical detections of the noncancerous and cancerous breast cells have been realized directly on the titatante nanowires-entangled bioscaffolds that were pre-grown on the titanium metal surface. Quantitatively, the titanate bioscaffold-based sensor has distinguished cancer cells from normal cells simply, directly, sensitively, and reproducibly for the first time. On this basis and again for the first time, the different cells' different metabolisms in glucose solutions have been differentiated electrochemically on the bioscaffold directly. These two sets of reproducible data have proven a new type of instant, simple and low-cost method for electrochemically fingerprinting, quantifying, detailing or tracing the microbiology of cancerous cells, stem cells, to name a few. This cell-sensor can be simply and generally applicable to upgrading of the common practices in the cancer pathology, and in monitoring in vitro and even in vivo tests at ultralow-cost and in real-time.

In some embodiments, electrochemically sensory nanofibers of titanate (a low-cost bioceramics) are grown first on a titanium metal, via a simple autoclave treatment. The bioscaffolds are then incubated with the indolent and deadly human breast cancer cells, and the normal breast cells, in both separate and mixed cases. The different cells have reproducibly shown significant differences in impedance change within certain frequencies on the sensory bioscaffolds. On this basis, different ratios of the cancer cells in the normal cells shifted the mixture's electrochemical signals quantitatively and reproducibly. This finding has suggested that the cancer cells have altered the bioscaffolds surface charge-density much more than the normal cells while binding to the surface of nanofibers of the bio scaffolds.

Embodiments of the invention have shown that the electrical conductivity of the titanate nanowire bioscaffold allows the identification of various types of cells based on the impedance of the titanate nanowire bioscaffold. For example, normal breast cells have a different impedance than breast cells that are cancerous, and breast cancer cells that are not very aggressive can be clearly distinguished from breast cancer cells that are very aggressive. This method of identifying types of cells based on the electrical characteristics of the titanate nanowire bioscaffold is quick, simple and inexpensive and is expected to have a large market in the field of medical diagnosis, as well as other possible applications where the rapid identification or discrimination of biological material is desirable.

In certain aspects, the process is measuring and discerning the small bio current response that separates cells based on their imbalance of homeostatic state, which causes them to emit a differential bioelectrical print that is a metric for identification of specific types and from other types. This bioscaffold process turns, selects, and directs electrochemical responses turning the bioscaffold into a cell sensor, which is the first of its kind worldwide.

Although there are other bioscaffold technologies and other impedance based methods, the collective modality of this bio scaffold technology is novel and reduces cost. According to the invention, the bioscaffold technology is used for cell growth, determinant models for cell population and growth, and studies that provide data for further studies of these populations. Among other things, the invention has at least the following advantages over the currently available methods.

This invention is measuring and discerning the small bio current response that separates cells based on their imbalance of homeostatic state, which causes them to emit a differential bioelectrical print that is a metric for identification of specific types and from other types.

This invention would be many times more cost effective and has a shorter and simpler production cycle than current techniques being used to discern between cell types.

Further, the novel nature of the process, using the bio-scaffold modality, allows the process to be utilized for other cell types and use; outside of the documented studies using known cancer cell types and known behaviors of the cells in response to current drugs and substances.

The process can also be used to determine efficacy of drug-based reaction related to cell behavior through the bioelectric signal differentiation techniques that are a part of this invention. This means that it can also be used in the drug discovery process, which could save vastly on cost and in turn reduce the price of drugs to the consumer.

In addition, the process can be utilized to test models of specific cell types such as animal and human subject bio-material, instead of using live animal and human subjects. This would be a huge win for entities being stalled by regulatory red tape.

According to the invention, the cell sensor does not need cell labels, and the process of differentiating types of cells is fast: within a few minutes for the entire sensing process, with low-cost, converting a small Ti-foil (similar to the stainless-steel foil in cost) via a simple one-step reaction. In addition, the cell sensors are mass-producible and easily fabricated: e.g., "cooking" in a pressurized container; water-washing; and drying in air. Moreover, the cell sensor and process can be used for selectively detecting different live cells' different metabolic wastes from digesting different nutrients (e.g., glucose) over the time; and selectively detecting different live cells' different metabolic wastes from reacting with different drugs (e.g., Doxorubicin, a cancer drug) over the time.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

Example

Impedance Sensing of Cancer Cells Directly on Sensory Bioscaffolds of Bioceramics Nanofibers In this exemplary study, TiO2 nanowires were used for the development of a label-free electrochemical biosensor on a bio-scaffold for direct detection of different live breast cancer cell lines (e.g., MCF7 and MDA-MB231) in vitro. Cancer cells exhibit altered local dielectric properties compared to normal cells. They have different electrical conductance and capacitance, which can be measured by electrical impedance scanning (EIS). Therefore, these observations open a new direction toward using the electrochemical properties of cancer cells and apply them to help in developing a prognostic tool for future diagnostic technology. This new method also can be potentially used in various important applications in cancer screening and monitoring, which are doable in vitro at ultra-low-cost and in real-time.

Materials

Titanium substrates (foil, 0.25 mm thick, 99.99% metal base) was acquired from the Alfa Aesar, USA. Sodium Hydroxide (NaOH) pellets from Avantor performance materials, Sweden. Glucose was obtained from Sigma-Aldrich, Inc., USA. Phosphate buffer saline (PBS) was prepared following the table:

TABLE 1

Regents for preparing PBS (pH 7.40, 1L)

| Chemical | Maas (g) |
|---|---|
| Sodium chloride (NaCl) | 8 g |
| Potassium chloride (KCl) | 0.2 g |
| Sodium phosphate dibasic ($Na_2HPO_4$) | 1.44 g |
| Potassium phosphate dibasic ($KH_2PO_4$) | 0.24 g |

An about 800 ml of deionized distilled (DDI) water was charged in a one-liter polyethylene bottle and stirred with a magnetic stirrer while adding the chemicals in the order (Table 1). The pH was adjusted to about 7.4 by titrating with a 1M HCl solution, the volume was adjusted to one litter, and the bottle was stored in a refrigerator at about 4° C.

Four cancer cell lines, MCF-10A, MCF7, MDA-MB231, and HCT116 (all from the ATCC, USA) were obtained from Dr. Du's and Dr. Shi's labs (the first three cell lines) and Dr. Muldoon's lab (the HCT116) on campus through collaborations. The MCF10A is a normal human epithelial cell line, MCF7 is a human non-invasive epithelial breast cancer cell line, MDA-MB231 is a human invasive epithelial breast cancer cell line. The HCT116 is a colon cancer cell line.

Hydrothermal Synthesis of $TiO_2$ Nanowire Scaffolds

Figure 2A:
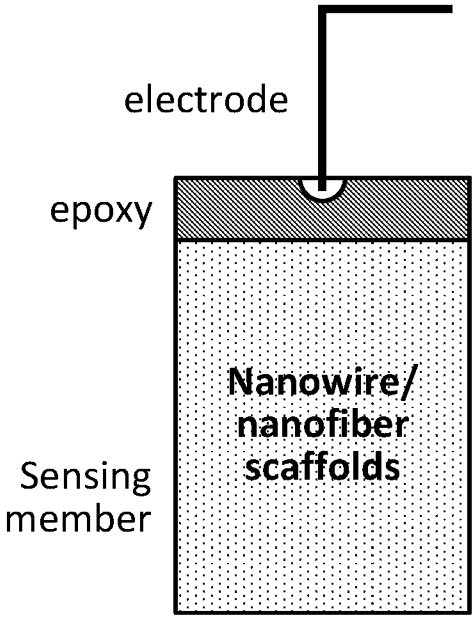
FIGS. 2A-2C show a schematic illustration of a sensor of titanate nanowire bioscaffolds (FIG. 2A) and a top surface of the titanate nanowire-scaffolds (FIG. 2B) and a cross-sectional view of the titanate nanowire-scaffolds (FIG. 2B), according to embodiments of the invention.
Figure 2B:
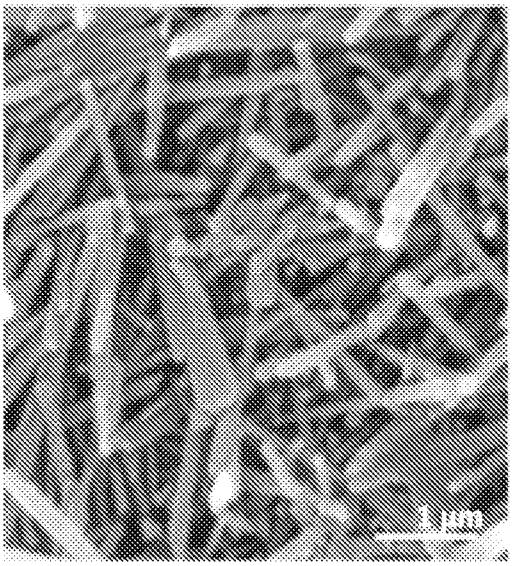
Figure 2C:
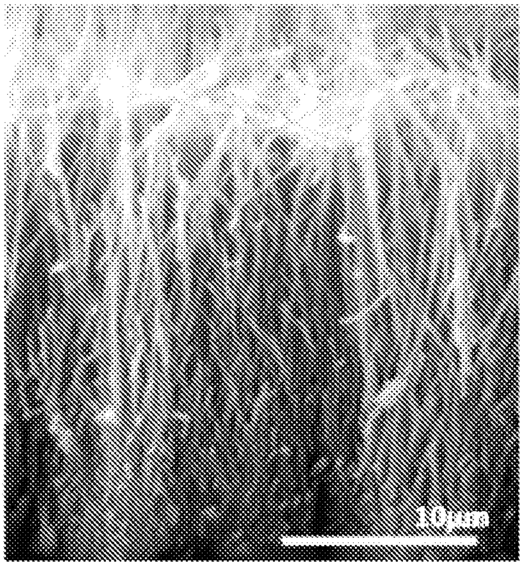

As shown in FIG. 1, a titanium sheet/plate (from Alfa Aesar) of about 1.5 cm×2.0 cm in size was sonicated in about 10 mL of acetone in a vessel for about 15 min at room temperature (25° C.), then taken out and rinsed with DDI water. Next, the Ti-sheet was placed in about 10 mL of 1.0 (M) NaOH solution in a Teflon-lined vessel (Parr Instruments) that was sealed and hydrothermally heated in an oven at 160-250° C. for 4-8 hrs, then cooled in air outside of the oven for 4-24 hours. Thus-treated sample now, surfaced fully with the titanate nanowires-entangled scaffolds, was rinsed with DDI water until the surface of the Ti-plate reached pH~7, and dried in air. Lastly, each sheet was scratched atop to expose metal for connecting the electrode, and epoxy-glued on rest edges and back, leaving a small area sensing cells, as shown in FIG. 2A.

The exemplary example illustrates the fabricating process of a single cell sensor only, Practically, the method can be utilized to fabricate a batch of cell sensors by providing a plurality of Ti plates/sheets. For example, the plurality of Ti-plates are simultaneously put in one autoclave container to let every plate surfaces to grow into the electrochemically sensory bioscaffold of bioceramic titanate nanowires.

Characterization of $TiO_2$ Nanowire Scaffolds

Powered X-Ray Diffraction (PXRD): The phase purity and crystalline structure of the nanowires were characterized by powered X-ray diffraction (PXRD) using Rigaku Miniflex X-ray diffractometer with a Cu Ka ($\lambda$=1.5405 Å) radiation source, scanning from angle 20 to 70 (2$\theta$) with a 0.02° step and a step time of 1.25 s.

Figure 4:
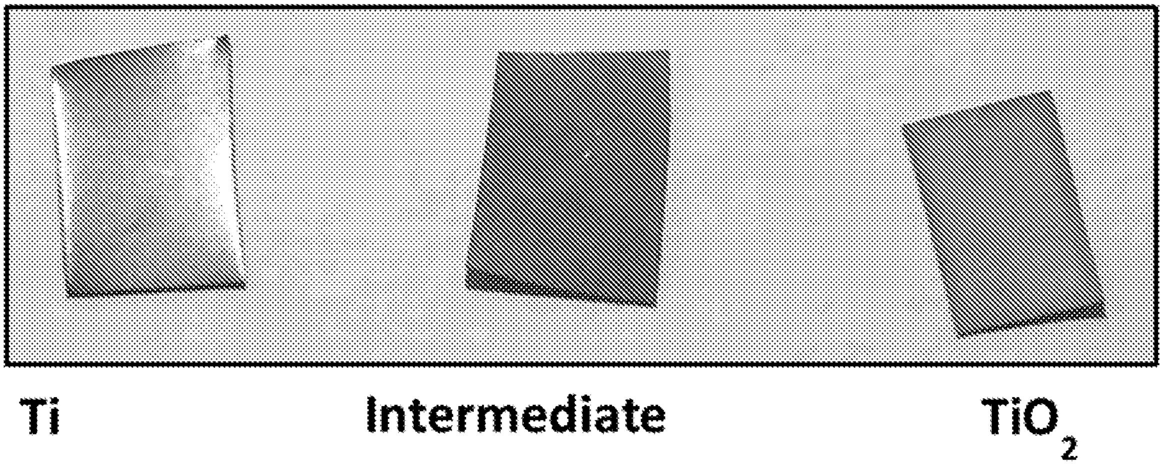
FIG. 4 shows the physical morphology of titanate after the hydrothermal treatment, according to embodiments of the invention.

As shown in FIG. 4, the intermediate sample (about 4 hrs reaction) looks dark grey, and the final product of the nanowire-covered surface seems grayish, both far from the Ti-metal that looks like the stainless steel. This implies that even the Ti-metal and nanowire should show different PXRD patterns.

Figure 5:
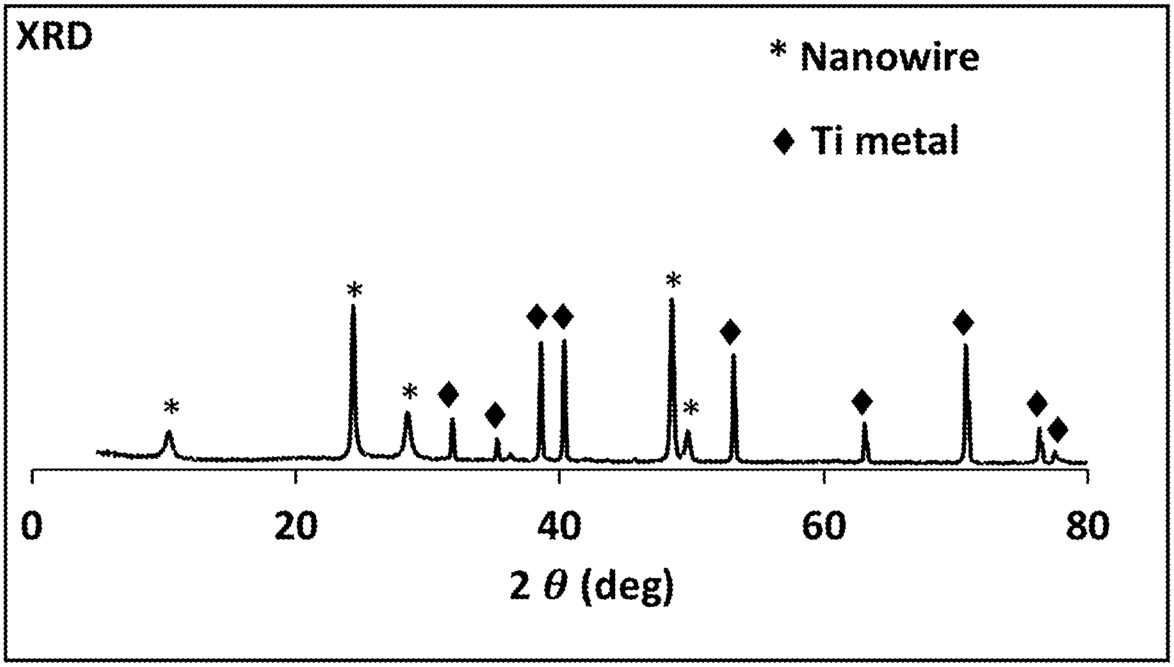
FIG. 5 shows PXRD pattern for titanate nanowire pattern of a sensor with titanate nanowires grown on the Ti-metal surface after 24 hours of the hydrothermal treatment, according to embodiments of the invention.

The PXRD study was conducted to characterize the crystallinity and structure of the nanowires grown directly on the Ti-metal surface. FIG. 5 shows the PXRD pattern of a typical sample with the nanowires grown in situ on the Ti-metal. The five peaks at the 2-theta values of 32, 34, 36, 38.5, 40, 53, 70, and 78 belong to the Ti-metal under the nanowires, while the rest peaks at the 2-theta values of 10, 24, 28, 48, 50 match the clay-like layered structure of sodium titanate ($Na_2Ti_3O_4$).

Scanning Electron Microscope (SEM): The morphology of the nanowire scaffolds was examined under a scanning electron microscope (SEM, Tescan SEM VEGAII SBH) performed at about 30 kV.

Figure 6:
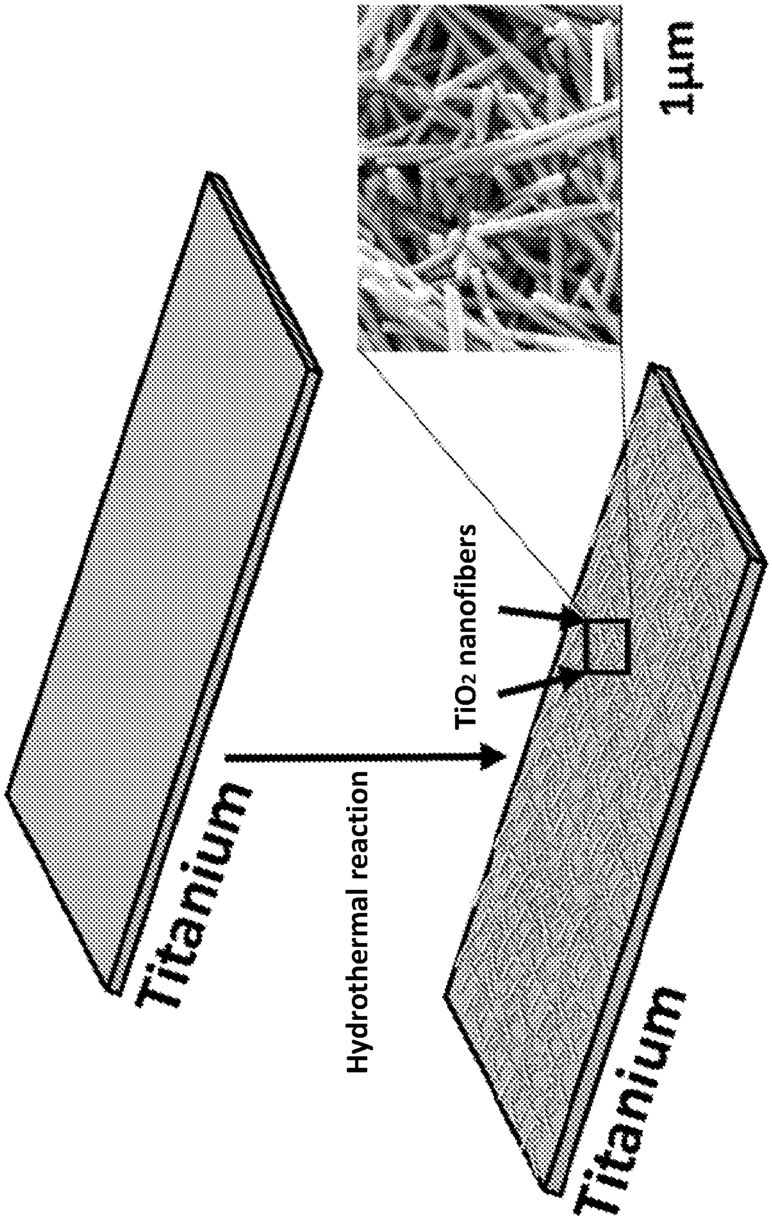
FIG. 6 shows a schematics for illustrating changes on the Ti-metal surface after the hydrothermal reaction, as supported by the SEM micrograph, according to embodiments of the invention.
Figure 7:
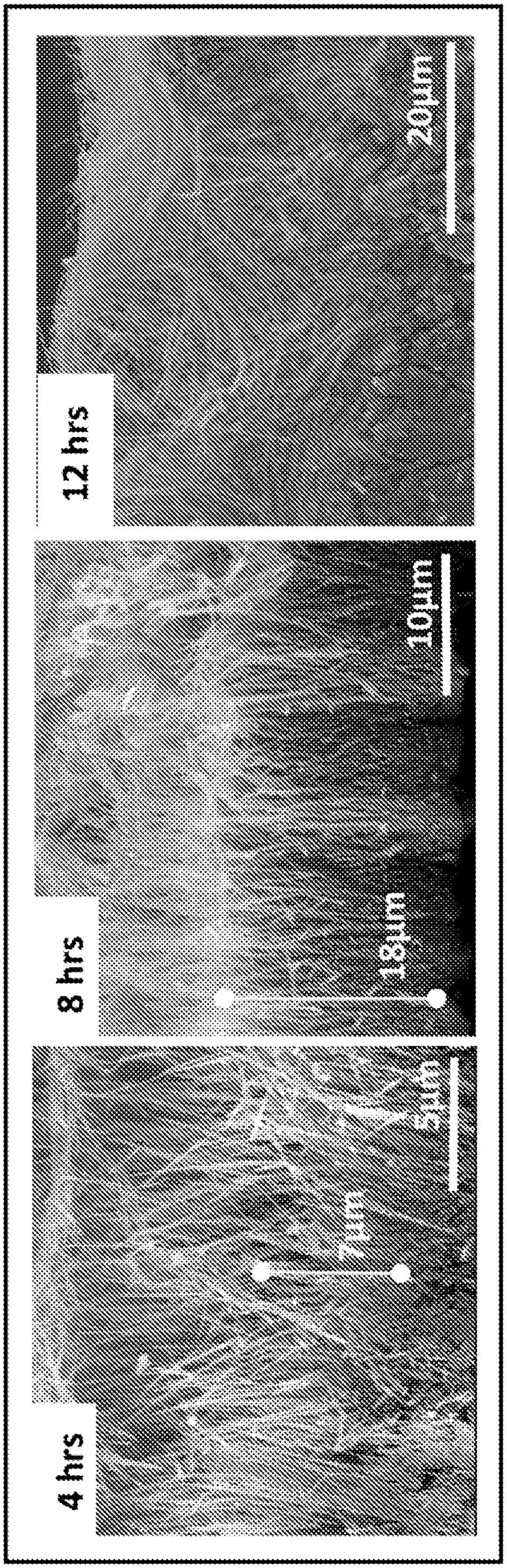
FIG. 7 shows SEM images of nanowires from the growths over the 4, 8, and 12 hours, according to embodiments of the invention.
Figure 8:
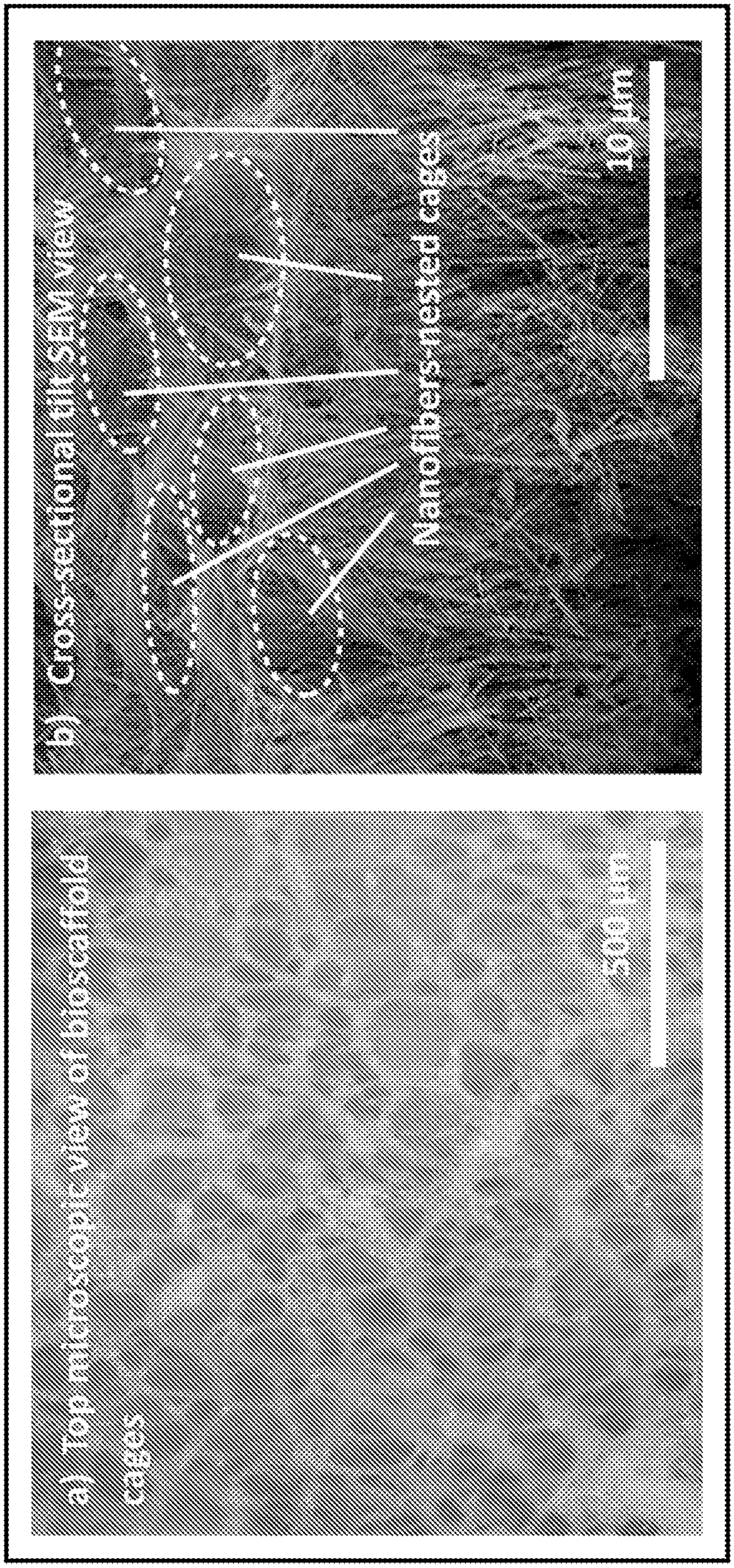
FIG. 8 shows SEM characterization of bioscaffolds on a Ti-metal substrate from 8-hour hydrothermal synthesis, according to embodiments of the invention. Left panel is a face-on view on the top of the substrate; and right panel is a tilt view of the top of the substrate.

As schematically illustrated in FIG. 6, the SEM micrographs illustrated the growth and entanglement of the nanowires in the hydrothermal reaction on the Ti-metal. After the hydrothermal treatment for about 4, 8, and 12 hours, the nanowires grew long enough over time to start to naturally entangle atop, self-assembling into the bioscaffolds with "bird-nest" like concaves (i.e., cell-nest cages) on the sample surface, as depicted in the cross-section images in FIG. 7. Further prolonging the reaction time to 7, 18, and 24 hours, respectively resulted in slightly better developed and organized cell-nest cages, as shown in FIG. 8. On this basis, the samples from 8-hours of the hydrothermal growth with enough well-developed "cell nests" were chosen to support the low-cost, quantitative, label-free, and real-time detections and differentiations of cancer cells for the first time on a smart bioscaffold.

Point-of-Zero-Change (PZC) on H(Na)-Titanate Nanowires: To estimate the PZC of the $TiO_2$ nanowires, a range of different pH from 2 to 12 were prepared by using 0.1 M of hydrochloric acid (HCL) and 0.1 M of sodium hydroxide (NaOH) in the DDI water. The pH was measured by a pH meter. The aqueous solutions containing the sample (i.e., Ti-metal sheet having $TiO_2$ nanowire scaffolds grown thereon) were rotating overnight at room temperature. The rotating allows the $TiO_2$ nanowires to be exposed to the different pH solution. The clear solution was used to measure the final pH using the pH meter and the result of initial and final pH were used to determine the PZC.

Figure 9:
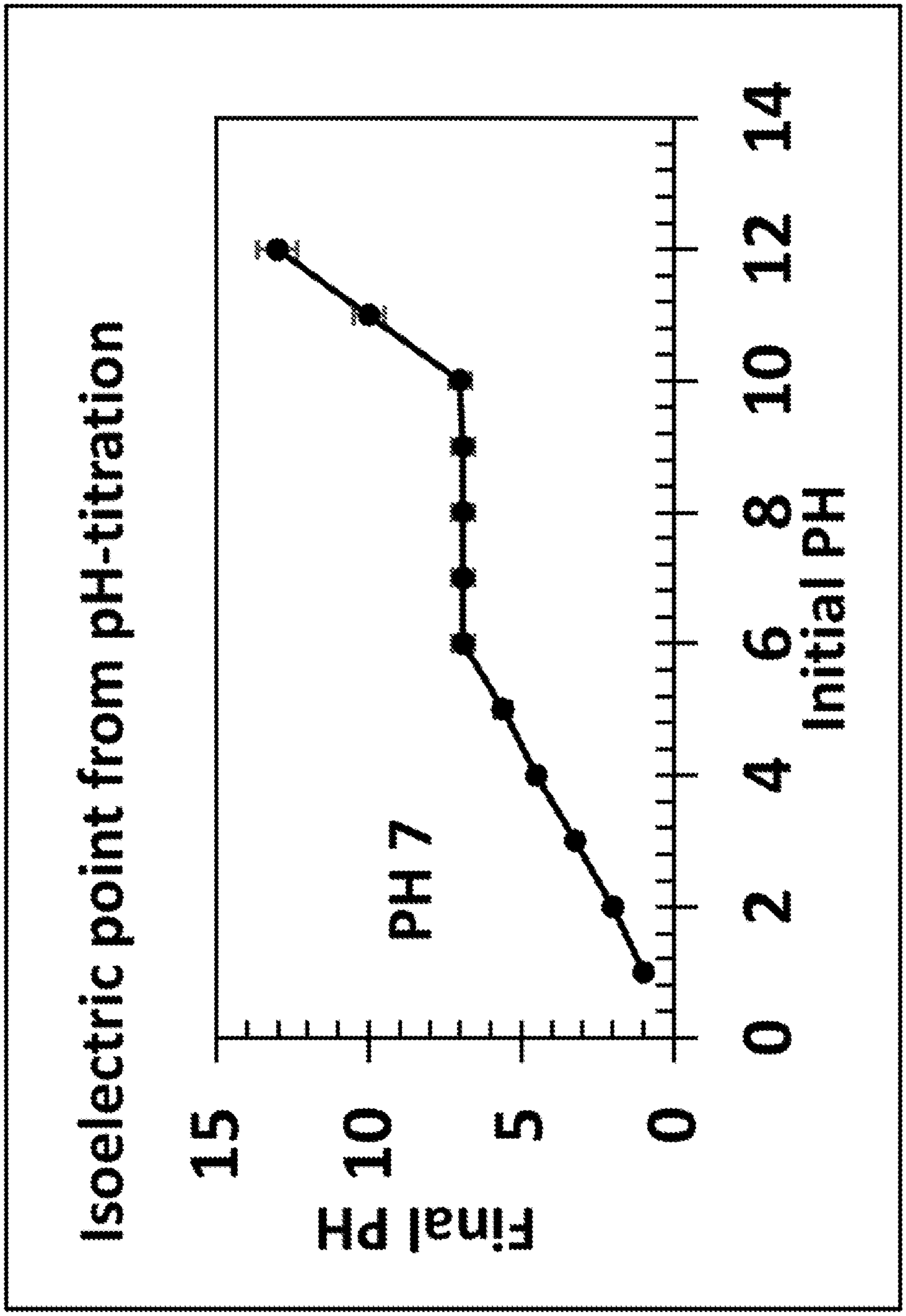
FIG. 9 shows a point of zero charge (Isoelectric point) for DDI washed titanate ($TiO_2$) nanowires from pH titration (1-12), according to embodiments of the invention.

To understand the surface cation exchange of titanate nanowires, a simple pH-titration was conducted to estimate, on the nanowire surface, the PZC value from the equilibrium between the $H^+$ on the nanowire surface and that in the solution. In the plot of the initial vs. final pH values shown in FIG. 9, the flat region's pH is often regarded as the PZC.

Accordingly, the nanowire's surface ion-exchanged protons ($H^+$) (i.e., Lewis acid) and surface hydroxide ($OH^-$) (i.e., Lewis base) groups can co-affect the average surface acidity/basicity at the nanowire-water interface. This further suggests (i) the continuous $H^+ \leftrightarrow Na^+$ ion-exchange can make the nanowire surface to buffer between pH=4 (of the hydrogen titanate) and pH=10 (of the sodium titanate), (ii) the capacity and kinetics of nano-buffering may reflect the completeness of intercalation of the $Na^+$ with the $H^+$ on the titanate nanowire, (iii) the negative framework made of $(Ti_3O_7)^{-2}$ tend to be a multi-deck Lewis base host, as $H^+$ is a strong but Na is a week Lewis-acid guest. This novel insight of the surface dynamics in the solution surface nanochemistry and "conjugated acid-base" nanochemistry supports that a controlled time (i.e., degree) of the DDI water washing (i.e., $H^+$ exchange) can convert the nests of as-made Na-titanate nanowires to that of a H(Na)-titanate nanowire with a PZC at/around the pH=7 for doing the cell-biosensing.

Figure 3:
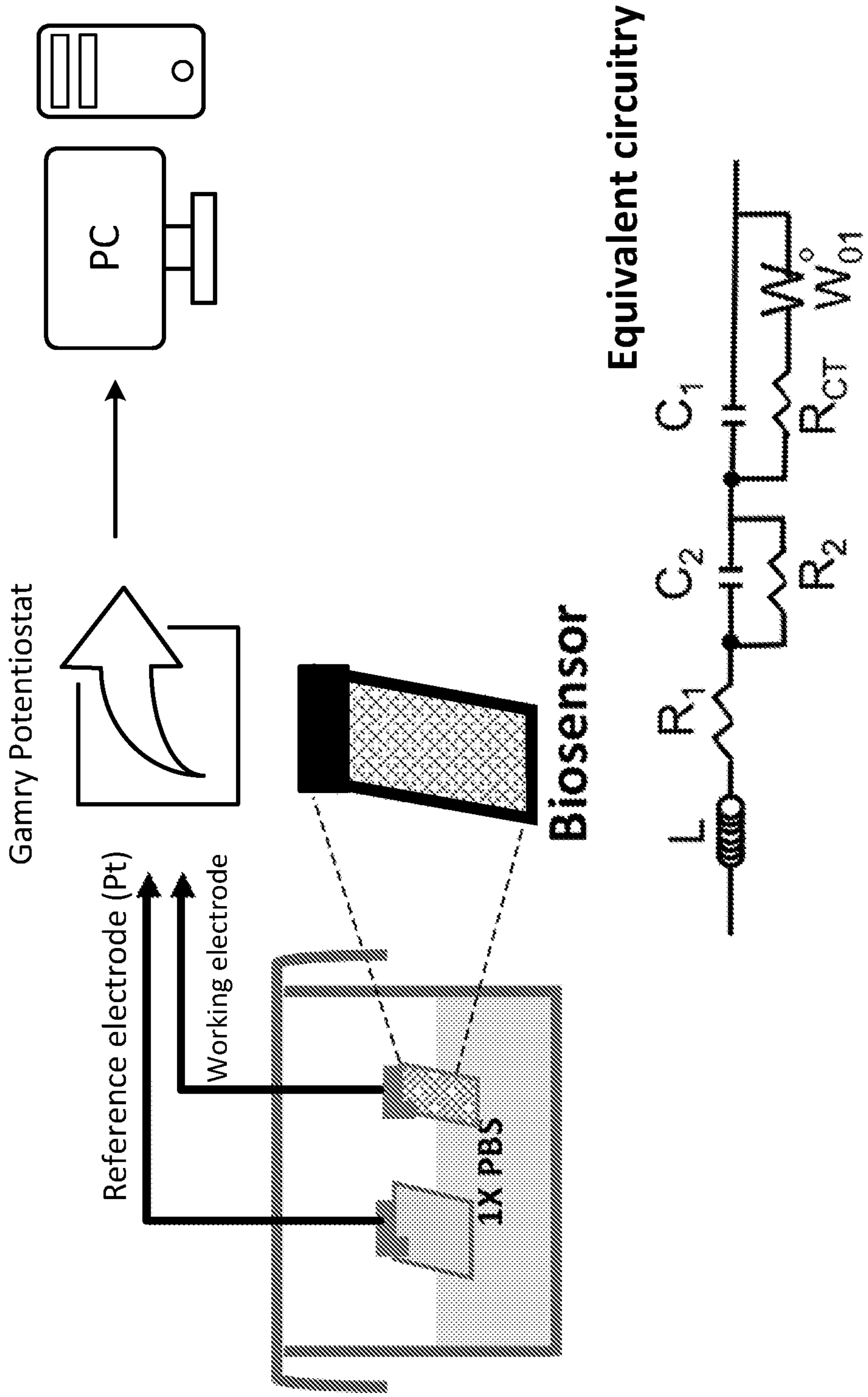
FIG. 3 shows a schematic illustration of a sensing set-up using the titanate nanowire bioscaffold sensor and corresponding equivalent circuitry, according to embodiments of the invention. The equivalent circuitry includes nanowire induction (L), nanowire resistance ($R_1$), cell membrane capacitance ($C_2$), cell membrane resistance ($R_2$), intracellular matrix capacitance ($C_1$), intracellular matrix resistance ($R_{CT}$), and Warburg diffusion impedance ($W_{01}$).

Impedance Characterization for Titanate Nanowires-Entangled Cell-Nests: One embodiment of the set-up for measuring the impedance of titanate nanowires-entangled cell-nests and its equivalent circuitry are schematically shown in FIG. 3. The biosensor is titanate nanowire scaffolds grown in the Ti sheet. The counter electrode is a platinum (Pt) electrode. The titanate scaffold sheet in a similar initial impedance curve was used as background. The impedance was measured by means of a Gamry Potentiostat (Reference 600, Gamry Instrument, USA), with the parameters of about 5 mV AC and frequency range about 0 Hz-1 MHz. The measured data were transmitted wiredly or wirelessly to a computer (PC) or a smart device for further processing and/or display.

Figure 10:
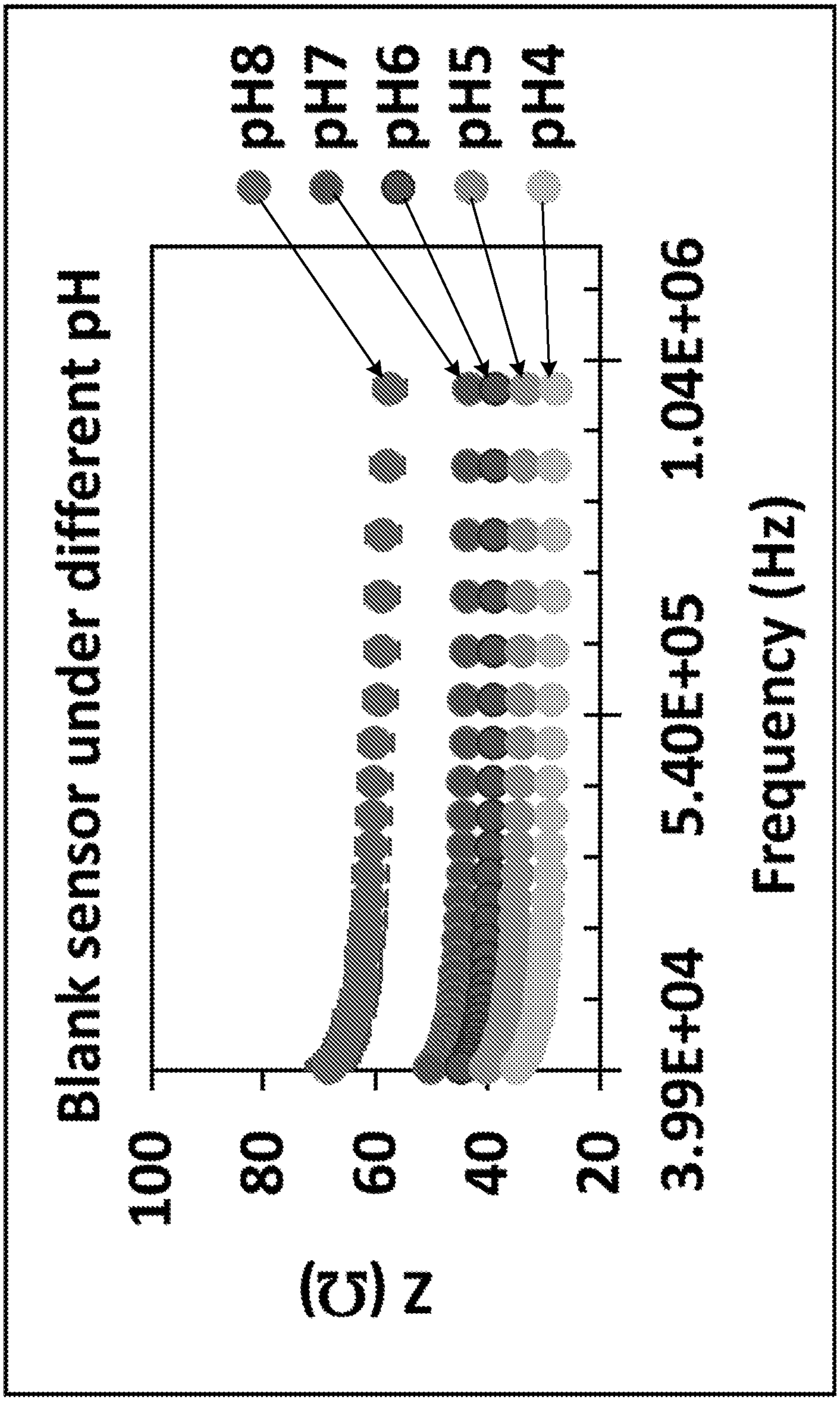
FIG. 10 shows impedance of titanate surface corresponding to pH titration, according to embodiments of the invention.
Figure 11:
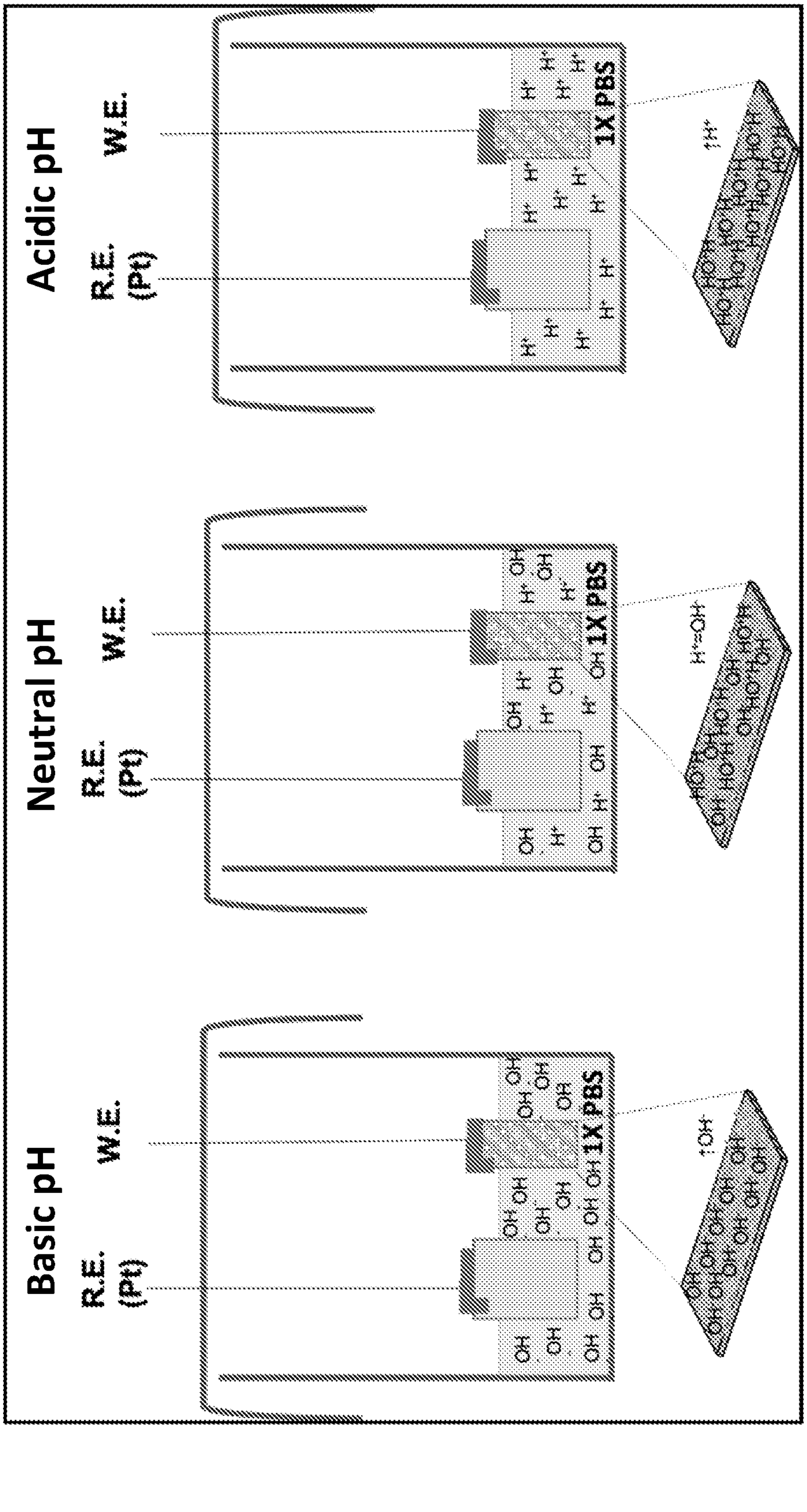
FIG. 11 shows a schematic illustration of surface deprotonation and protonation corresponding to the aqueous solution pH change during sensing, according to embodiments of the invention.

A series of (1×) PBS solutions between pH 4 and pH 8 were used to quantify the effect of pH on the impedance of the titanate nanowires-entangled cell-nest (FIG. 8). The result shows a clear correlation between the impedance and solution pH, in which the impedance increases generally with the pH. This correlation can be explained again with the Lewis acid/base theory. As shown in FIG. 11, in the aqueous solution, the hydroxyl group on the nanowire surface was deprotonated and negatively charged when the pH~7 (i.e., above the PZC point). On the contrary, the surface —OH groups being protonated (gain $H^+$) are positively charged at the pH less than PZC point. This is in line with such a fact that an oxide is in an aqueous solution above (or below) its PZC, the surface pH decreases (or increases) as the surface be deprotonated (or protonated). At equilibrium, no net proton transfer thus no further change to the PZC point. Thus, the electrical impedance of the nanowires (with the poor electrical conductivity) is commonly used to quantify such surface-PZC point shifting corresponding to the mass transfer of ions of any type in a confined area. Equivalently, when the solution pH decreases, the nanowire surface is more protonated, gaining more positive charges on the nanowire surface to facilitate a faster charge-transfer along the nanowire surface and to reduce the impedance. This supports FIG. 10 and in turn how crucial the water-washing step in controlling the nanowire surface PZC point.

Impedance Sensing of Live Cell on $TiO_2$ Nanowires

Characterizing individual cancerous cells from the blood stream, i.e., the circulating tumor cells (CTC) tumors using a simple and quick impedance test is of importance to support both qualitative and quantitative cancer pathology beyond the current practices using either staining or optical imaging that are slow, labor-intensive and expensive. Cancer cells of the malignant and benign subtypes look similar from one another using the staining and optical imaging. However, the subtypes difference in metabolism should enable one to develop an alternative diagnostic tool with negligible false-negative and false-positive problems, which has been underexploited. Such novel method should rely on the cancer cells' metabolic wastes among which the ionic spices can change the nanowire-bioscaffold surface's charge-transfer pattern, thereby affording the novel cell-sensing method.

Electrochemical Impedance Spectroscopy (EIS) is a well-established method widely used in biosensing, using an alternative current (AC) to detect electrochemical impedance. The impedance is defined as the ability of circuit to resist the flow of electrical current in a complex system, for measuring over a wide range of AC frequencies the dielectric properties of a material. EIS has been used in this work to develop a label free biosensor that hopefully can distinguish multiple electrochemical changes occurring at the same time. For example, it may identify the diffusion-limit of a passive film and the electron transfer rate of a reaction, the capacitive behavior of the system, etc. In the impedance sensing experiment, an AC voltage signal is applied as a frequency-dependent excitation. Then, a response is measured.

FIG. 3 shows schematically one embodiment of the setup for cell sensing using the titanate nanowire bioscaffold sensor and corresponding equivalent circuitry. In the setup, the biosensor is the titanate nanowire scaffolds grown in the Ti sheet. The counter electrode is a platinum (Pt) electrode. Both the biosensor and the counter electrode are placed in the PBS solution containing cells. A Gamry potentiostat is coupled to the biosensor and the counter electrode for measuring electrical characteristics such as the electrochemical impedance. The measured data were transmitted wiredly or wirelessly to a computer (PC) or a smart device for further processing and/or display. The equivalent circuitry includes nanowire induction (L), nanowire resistance ($R_1$), cell membrane capacitance ($C_2$), cell membrane resistance ($R_2$), intracellular matrix capacitance ($C_1$), intracellular matrix resistance ($R_{CT}$), and Warburg diffusion impedance ($W_{01}$). The impedance of the equivalent circuit is given by:

$$Z = j\omega L + R_1 + \frac{R_2 \frac{1}{j\omega C_2}}{R_2 + \frac{1}{j\omega C_2}} + \frac{(R_{CT} + Z_\omega)\frac{1}{j\omega C_1}}{(R_{CT} + Z_\omega) + \frac{1}{j\omega C_1}}$$

where $j=\sqrt{-1}$, $\omega=2\pi f$, f is the frequency of the AC voltage signal is applied. Warburg impedance diffusion $Z_\omega$, is described by:

$$Z_\omega = \frac{\sigma}{\omega^{1/2}} - \frac{j}{\sigma\omega^{1/2}}$$

where $\sigma$ is related to the diffusion coefficient of species in the cell.

In the exemplary study disclosed herein, all experiments were repeated three times using the same $TiO_2$ nanowire scaffold. All cell suspension contained the same cell number/ml. All data were expressed as mean±standard deviation for at least three repeats.

Impedance Measurement for Cancer Cell Lines: This measurement was carried out to determine if the bio sensor can distinguish the cancer cells pathological malignance. The frequency was swept to determine range giving the clear impedance difference (separation) between the cancer and normal cell line. At least three such biosensors having similar initial impedance curve were incubated in an about 10 ml (1×PBS) solution containing one million ($10^6$) cells/ml for about 35 minutes at room temperature (about 25° C.), with each of the three breast cells lines (MCF10A, MCF7 and MDA-MB231) and one colon cancer cell line (HCT116), respectively.

Impedance Measurement for Breast Cancer Cell Lines over the Sensing Time: Cells were incubated in different time intervals (about 25, 35, and 45 minutes). The impedance was recorded for the three cell lines (e.g., MCF10A, MCF7, and MDA-MB231) to determine the best incubation time to do the impedance test as described earlier. The parameters setup was by changing the frequency starting from about 30 kHz to about 1 MHz.

Cells contain an intracellular medium surrounded by a semipermeable membrane, which separates the extracellular from the intracellular ionic solutions using the cell membrane made from a lipid bilayer, proteins, and some polysaccharides. The membrane exhibits capacitive properties due to the electrical potential difference between the membrane's two sides, and the impedance of cell membrane's capacitance changes with the frequency. At low frequency, the cell membrane is more like an insulator, resulting a higher impedance (i.e., highly resistivity) that allows current in the extracellular medium. When the frequency is high, the cell membrane is like a capacitor and starts to conduct charges and allow the current to go through the membrane, thus-reducing the impedance signal.

Figure 12:
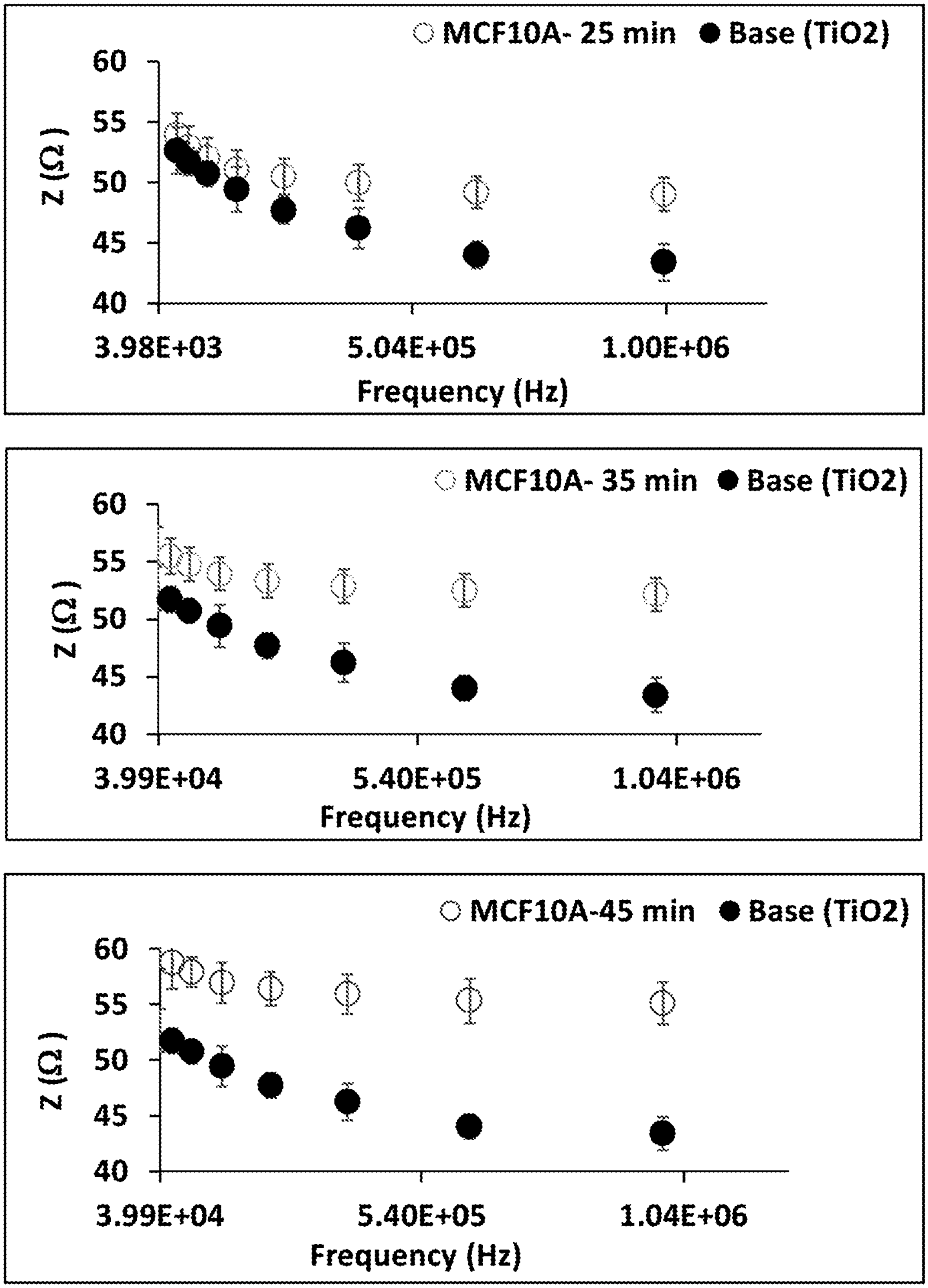
FIG. 12 shows impedance vs frequency for normal cells (MCF10A) in three-time sensing durations (25, 35, and 45 minutes), according to embodiments of the invention. The error bar reflects three repeats.
Figure 13:
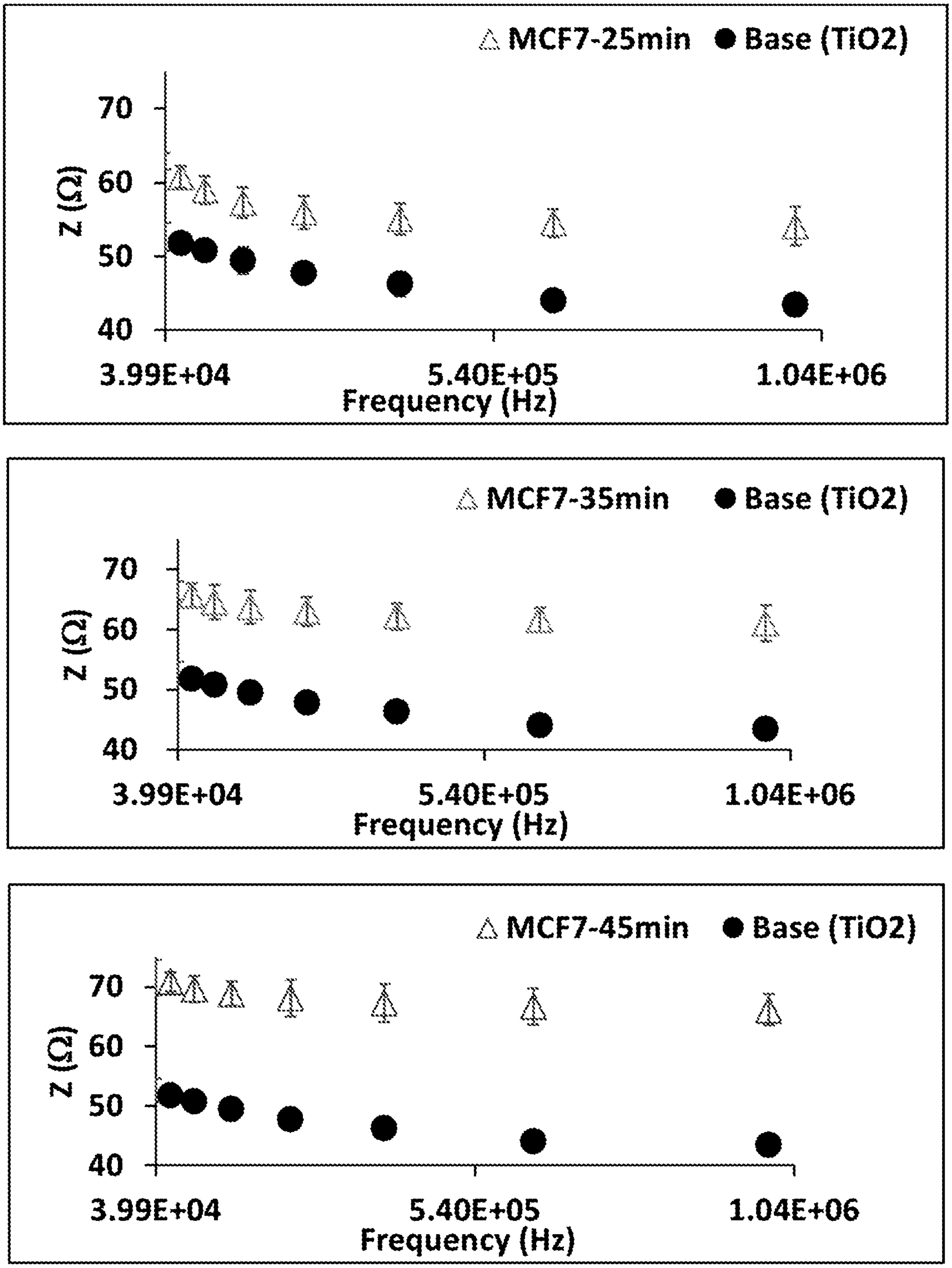
FIG. 13 shows impedance vs frequency for benign cancer cells (MCF7) in three-time sensing durations (25, 35, and 45 minutes), according to embodiments of the invention. The error bar reflects three repeats.
Figure 14:
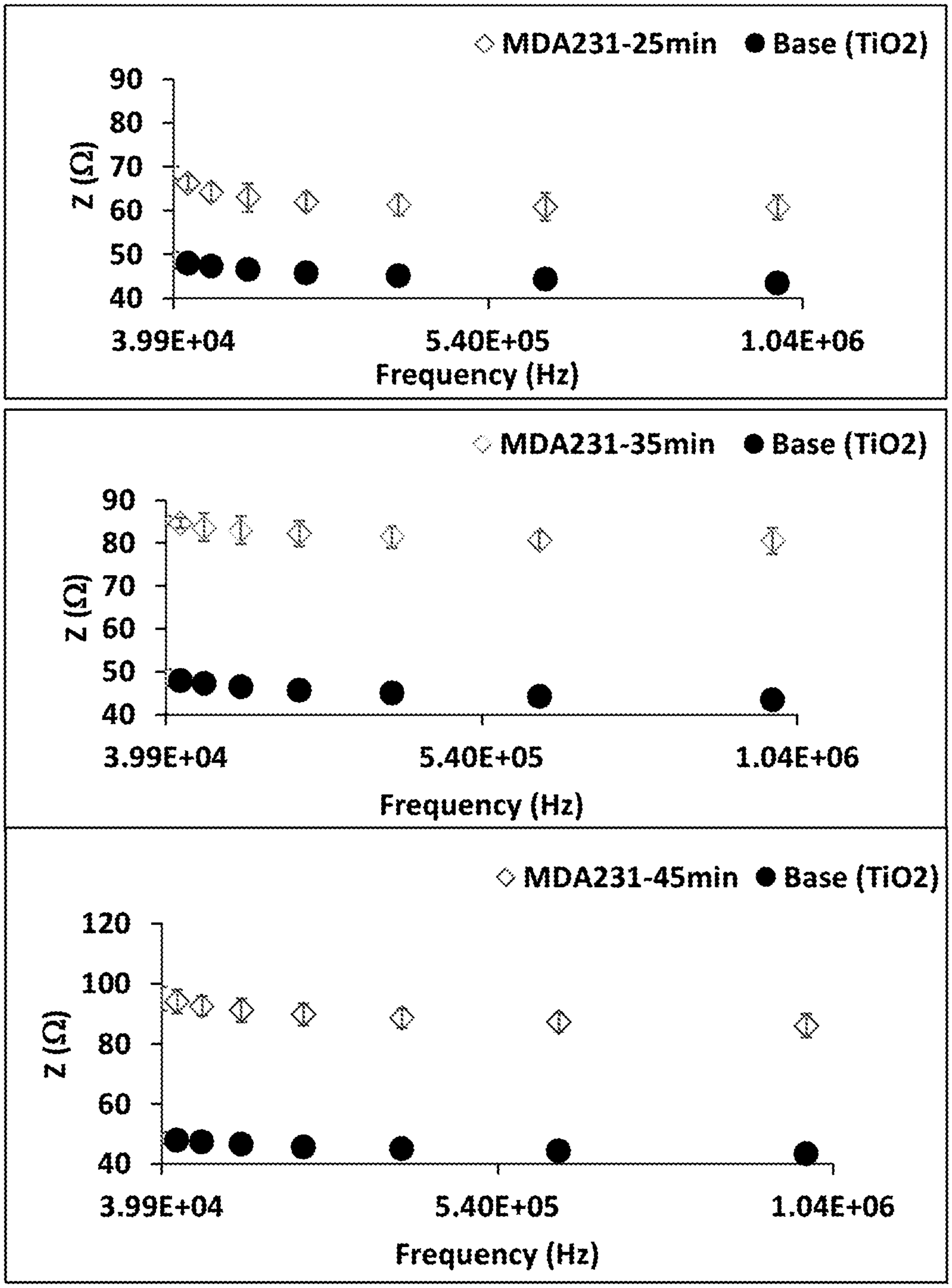
FIG. 14 shows impedance vs frequency for malignant breast cancer cells (MDA-MB231) three-time sensing durations (25, 35, and 45 minutes), according to embodiments of the invention. The error bar reflects the three repeats.
Figure 15:
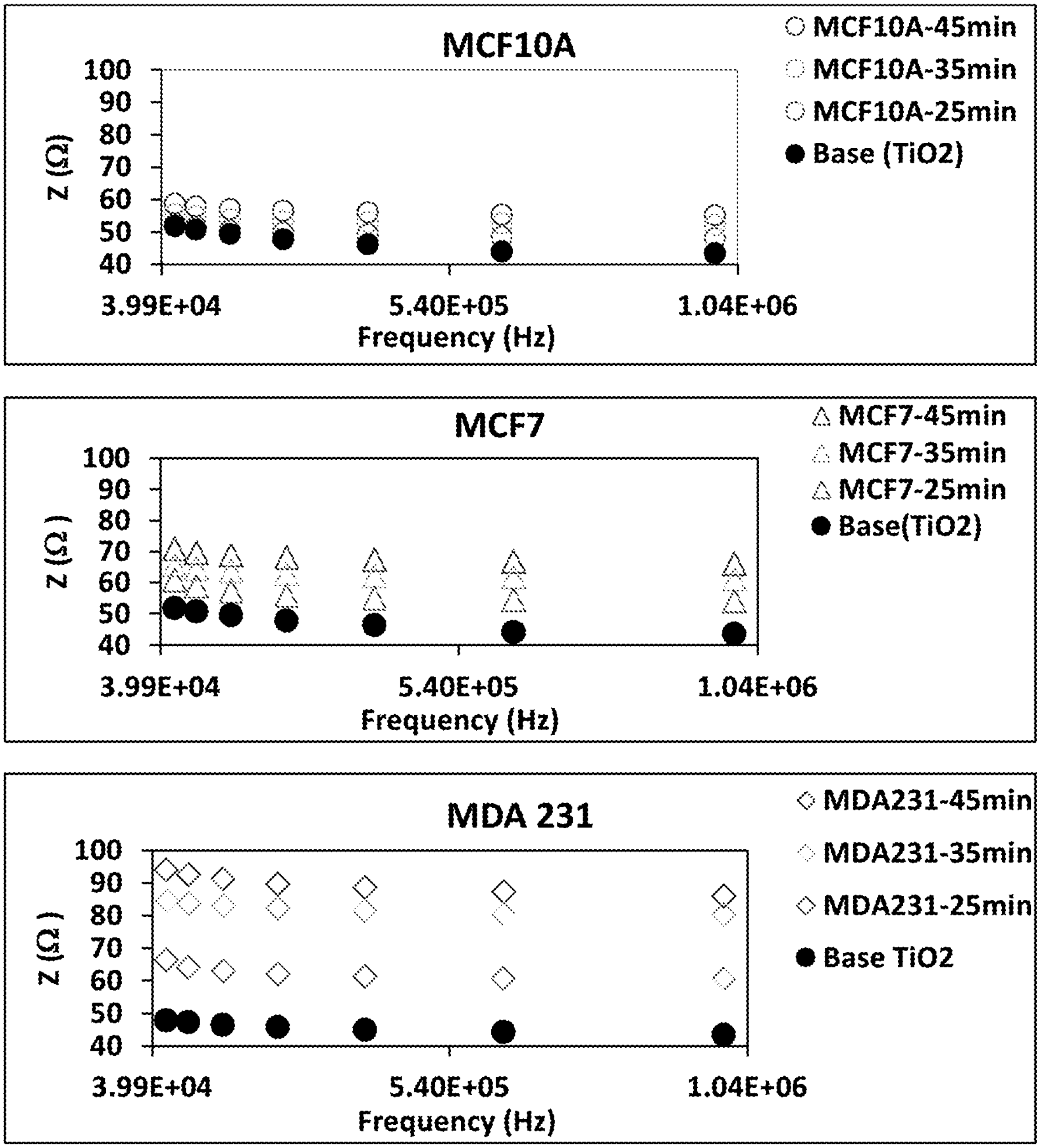
FIG. 15 shows impedance vs frequency for three breast cancer cells (MCF10A, MCF7, MDA-MB231) in three-time duration (25, 35, and 45 minutes), according to embodiments of the invention.

In the experiment, more cells were attached onto the nesting nanowires over long time after the bioscaffold-sensor was inserted in the PBS solution containing the cells. Different cells upon attaching onto the nanowire-nest surface can instantly change the nanowires' impedance differently. After the attaching for about 35 minutes, normal breast cells (MCF10A) shift the impedance by about 40-50 ohms at the high frequency range (1 MHz) (FIG. 12), while the benign breast cancer cells (MCF7) shift that to about 60 ohms (FIG. 13), and the malignant breast cancer cells (MAD 253) can do so by about 80 ohms (FIG. 14). The impedances shown in FIG. 14 suggest that the net surface charge for the three cell lines are different, therefore, they change the nanowires surface charge differently, which can be better seen in thus-combined in FIG. 15.

Figure 16:
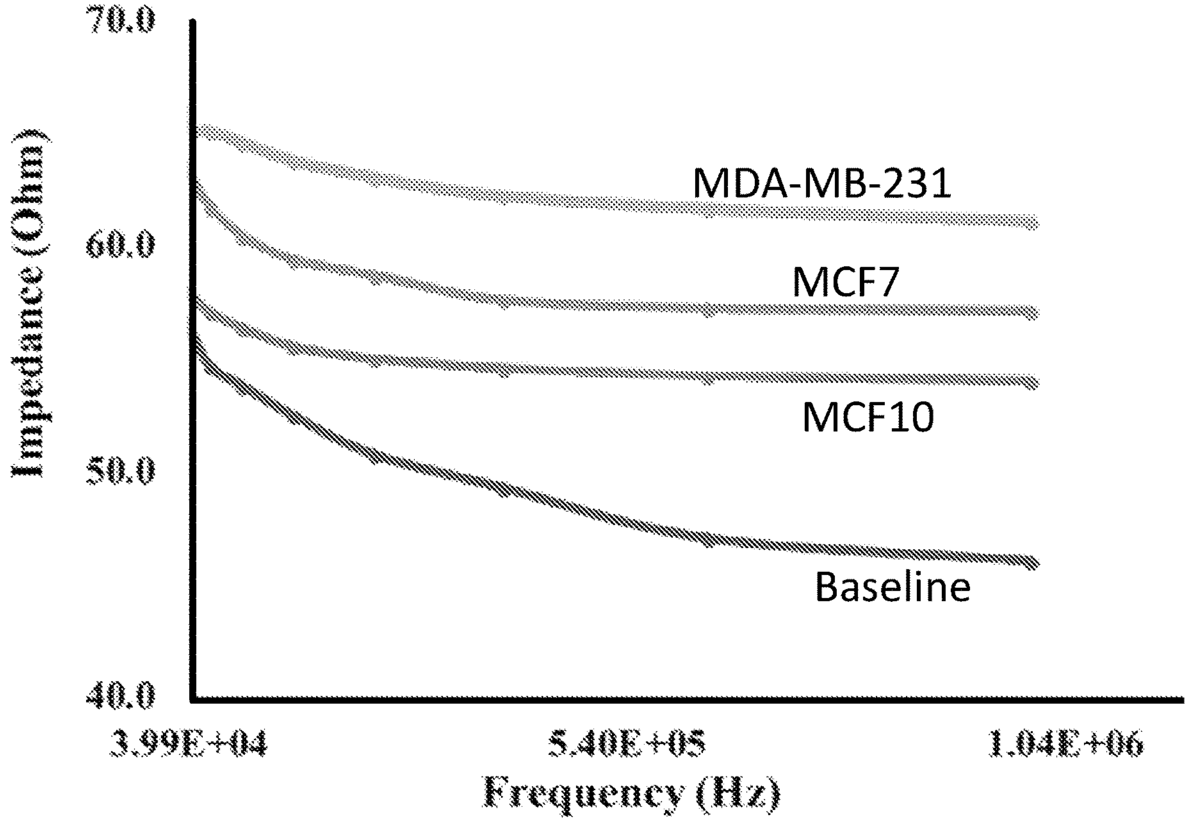
FIG. 16 shows impedance measurements of MCF-10A, MCF-7, and MDA-MB-231 over a frequency range (30 KHz-1.0 MHz), according to embodiments of the invention. The experiment was tripled and the average with standard deviations are calculated.

FIG. 16 shows averaged impedances of MCF-10A, MCF-7 and MDA-MB-231 over the frequency range from about 30 KHz to about 1.0 MHz, with standard deviations. Each measurement was repeated three times.

Dobrzynska and coworkers did the electrophoresis to study the changes of surface electrical properties as a function of pH for the same cell lines, on a four-component equilibrium model with a negligible variation between the experimental and theoretical charge in the pH range of 2.5-9.0. In studying the mammalian cells, the pH was kept narrowly between 6 and 8, outside which the cell membrane proteins can be maintained during the electrophoresis. The results revealed that at a lower pH the charge density on the cancer cells surface gets more positive, meaning more protonated. Their findings concluded that this increase is related to the acidic ($C_{TA}$) and basic ($C_{TB}$) functional groups' average association constant for hydroxyl ions ($K_{OH}$) in the breast cancer cell membrane, especially in MDA 231, which is higher than that in normal cell (i.e., MCF10A) membrane.

From the plasma membrane proteomics, the cell membrane proteins are elevated in MDA 231, comparing with the MCF7 and normal (MCF10A) cells, and the keratin type I Cytoskeletal 17 (KRT17) is present only in the normal cell. As the cell turns malignant, this cytoskeletal filament disappears i.e., being replaced by Keratin type I Cytoskeletal 19 (KRT19) that was found to be higher in the MCF7 cell-membrane. Vimentin (VIM), a cytoskeletal filament mostly expressed in mesenchymal stem cells, is highly expressed in the aggressive cancer cell (MDA-MB231). Microtubule-interacting protein 1B (MAP1B) was only found in MDA-MB231, while the subtype (MAP4) was found in both MCF7 and MCF10A. Myosin regulatory light chain 12B (MYL12B), important in maintaining the cell structure, was found only in MDA-MB231. Further, the MDA-MB231 have more cytoskeletal filaments and some are abnormally expressed. These are important to cause the resistivity changes by lowering the water content in the cell. These variations can be measured using the impedance to quantify the mass-transfer outside the cells at low frequency and that across the cell membrane (e.g., into the cytoplasm) at high frequency.

Further, the lipid bilayer was investigated to show the cancer cell membrane with fewer fatty acids and phospholipid types. Interestingly, that study found that cancer cells produce more positively charged phospholipids, e.g., (PE 36:2) in MCF7 and (PC 32:0, PC 36:2, P I 36:1) in MDA-MB231. Among the fatty acids, mostly are the oleic acid (C18:1) and palmitoleic acid (C16:0) in MCF7, and the oleic acid (C18:0) and docosahexaenoic acid (C22:6) in MDA-MB231. The presence of such unsaturated fatty acids within the cell-membrane bilayer increases the cell membrane's fluidity, flexibility, and permeability along with the pathological malignancy of the cancer cell. An elevated phospholipid production in the same cell-lines was reported. This overproduction is often correlated to a tumorigenic transformation. This is because in the tumor's external microenvironment, the pH is more acidic (pH 6.5) hence the cancer cell surface net-charge is more positive, as the surface carboxyl, amino and phosphate groups are protonated. Therefore, increasing the number of cell surface phospholipids lead to a more negative surface charge density at high pH but a more positive charge density at low pH.

In breast tumor, the sialic acid was lately found to be upregulated which affects the cell membrane charge, and in turn the acid and basic groups on the cell membrane. Thus, a knock out to an important gene in the sialic acid metabolism disabled the production of the active form of sialic acid and helped lower the lung cancer metastasis rate in vivo.

In addition, the reactive oxygen species (ROS) can affect membrane lipids and proteins in the acidic environment, via triggering a lipid peroxidation process. Consequently, phospholipids in the inner lipid layer such as phosphatidylserine (PS) expose to the outside, thus-increasing both the acid group's content on the cell surface, and the level of $K_{BOH}$ comparing with the original cell-membrane.

All these reports in the literature consistently support that the transformation in cell membrane structural lipid and protein composition can cause the increase in resistivity due to exposure of negatively charged groups. In turn, the higher resistivity can lower the cell's outer layer potential, which further increases the resistivity of the cancer cell membrane and supports the selective quantitative cell-sensing and cell-type characterization.

Figure 17:
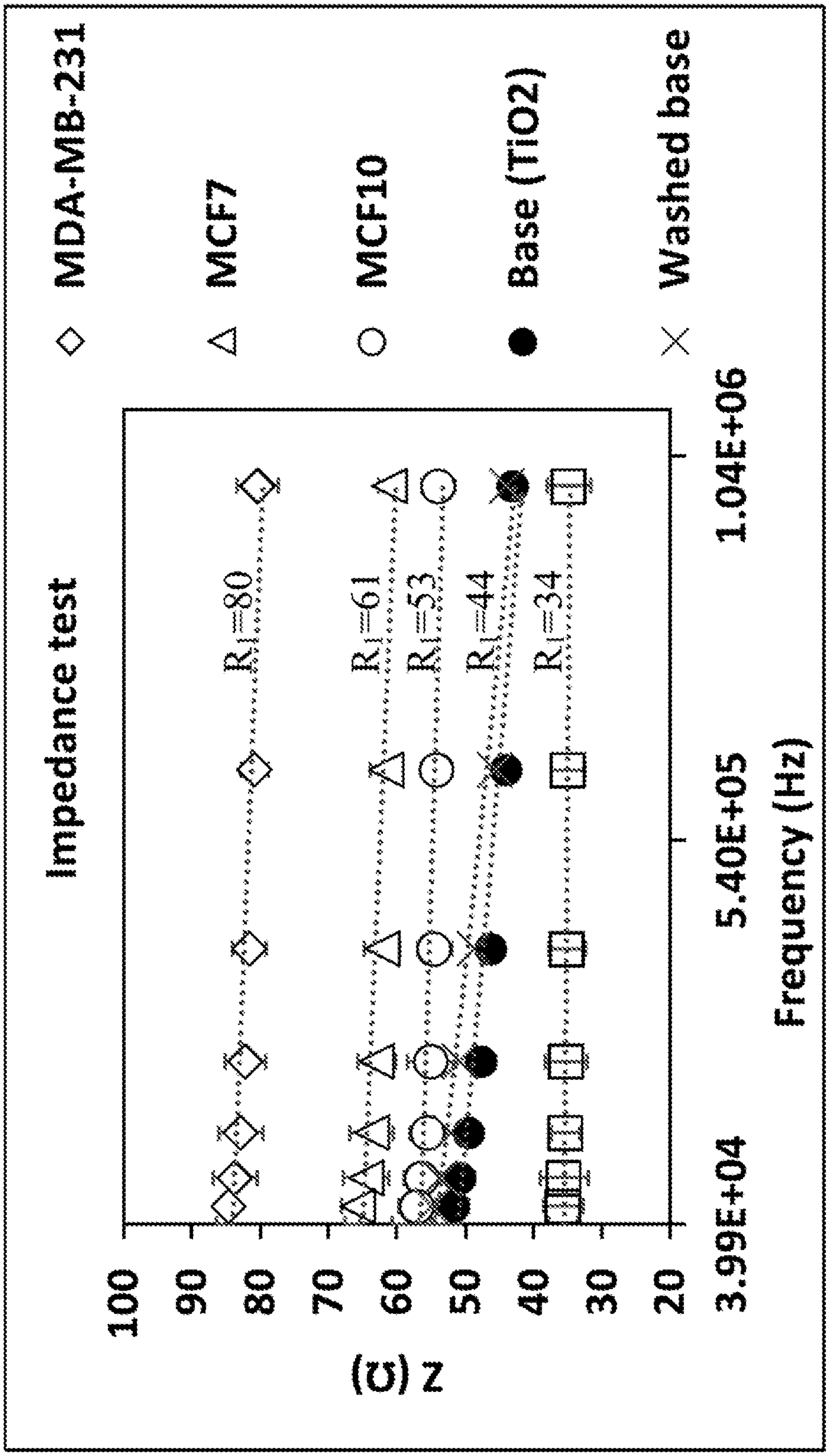
FIG. 17 shows impedance for normal cell and different cancer cell types, according to embodiments of the invention. MDA-MB-231 breast cancer cells, MCF7 breast cancer cells, MCF10 mammary epithelial cells.

Impedance Measurement for Distinguishing Breast Cancer Cells from Colon Cancer Cells: An important question to be answered is whether there is a difference in the surface charge density of cancer cells developed in different part of the body, e.g., colon cancer cells vs. breast cancer cells (FIG. 17). The breast cancer cells showed an increase in the impedance level corresponding to the cell's pathological malignancy. However, an opposite response was observed from the same sensing of an aggressive colon cancer cell (HCT116) on the same set of the biosensors. This HCT116 cell line has turned the nanowire-surface to be more conducting from apparently a lower impedance level. With little being reported in literature based on our thorough literature survey, the impedance data can guide future cell-biology study on the proteins and lipids in the HCT116 cell's membrane that are different than that in the breast cancer cells'. Further, modifying the breast cancer cell line membrane's protein and lipid constitution may help tell what opposite charge density is in the HCT116 cell with, probably, more amino groups on its surface at the experimental pH 7.4 being protonated to hold a positive net surface charge thus-making the bioscaffold-nanowire to be more conducting. Since the breast tissue (neutral) have different pH in nature than the colon (basic), the colon cancer cells should easily adapt to the acidic environment generated by the tumor tissue.

Figure 18:
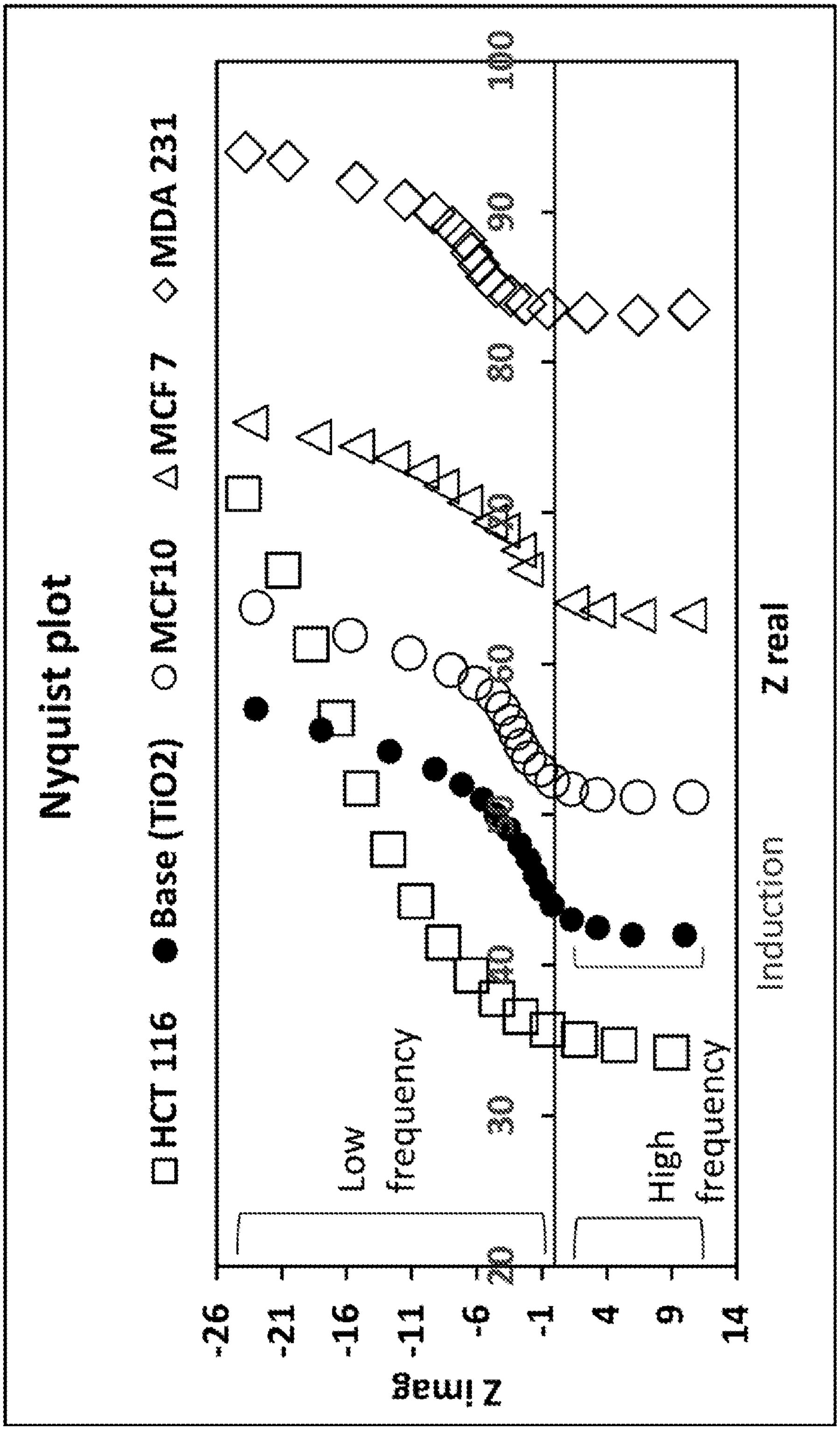
FIG. 18 shows Nyquist plot for $TiO_2$, normal (MCF10A), and three different cancer cell lines, according to embodiments of the invention.
Figure 19:
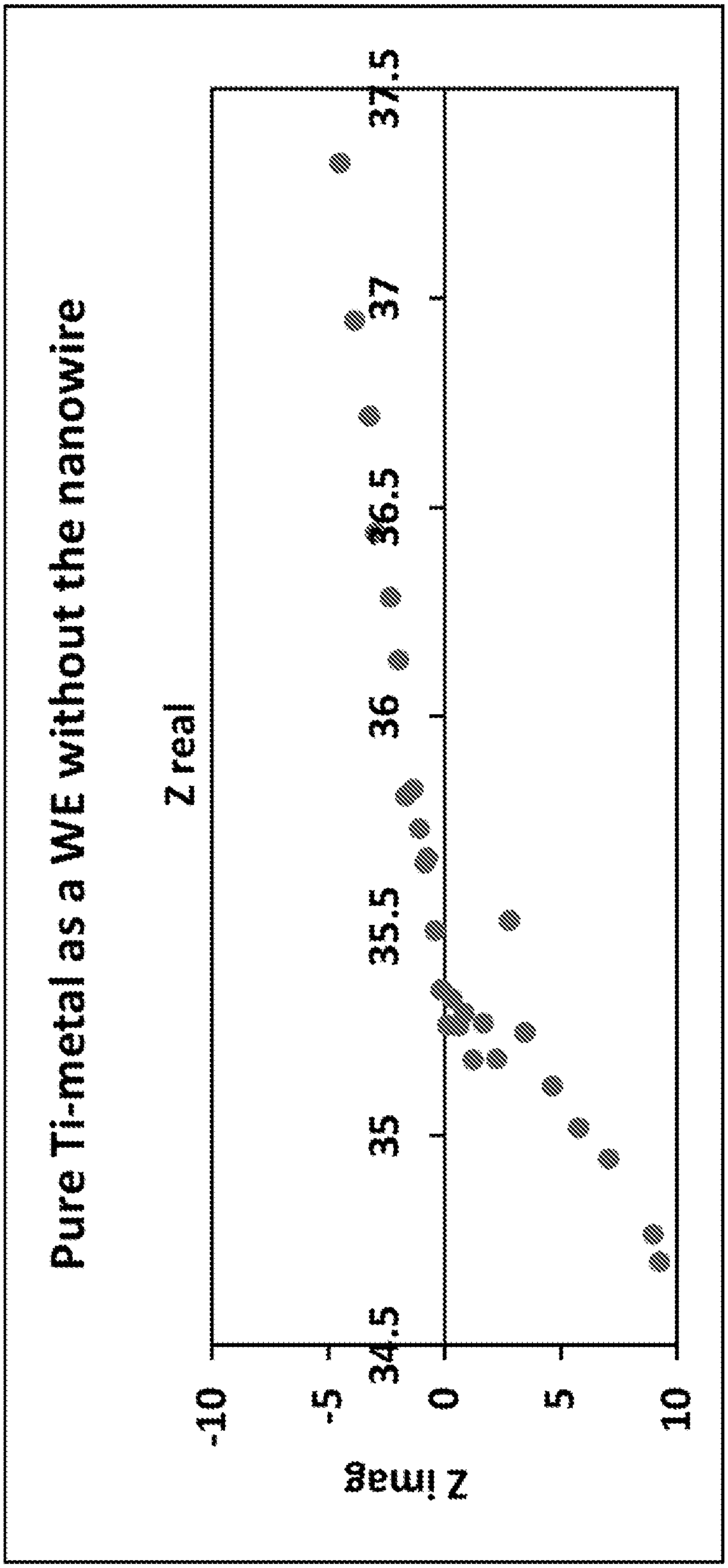
FIG. 19 shows Nyquist plot for a titanium metal.

In the Nyquist plot shown FIG. 18 with the real ($Z_{RE}$) and imaginary ($Z_{IM}$) parts of the complex impedance, each cell-line has a characteristic impedance level. Unusually, an induction effect exhibits clearly on every thus-made bio scaffold, due apparently to the nesting nanowires circularly self-assembling into each nest. In other words, the current moves on each nanowire surface from the bottom to the top of the nanowire in a circular manner for spirally electric field reaching the surface of each nest, thus-creating an inductive electromagnetic field for the nano-induction effect. This effect was not observed in pure Ti-metal working electrode, which means that the induction is not generated from the leads, as shown in FIG. 19.

Impedance Measurement for Breast Cancer Cell and Normal Cell Lines in Different Mixing Ratios: This is to determine if the biosensor can detect the presence of abnormal cells within the normal population and can distinguish the pathological stage of cancer cell and how the impedance signal would change when the breast cancer cells and normal cells be mixed together. Both cancer cells lines (e.g., MCF7 and MDA 231) where mixed with normal cell line (MCF10A) in different (cancer cell: normal cell) ratios (1:1000, 1:100, 1:50, 1:25, 1:10, 1:5). The parameters setup was by changing the frequency starting from about 30 kHz to about 1 MHz.

Figure 20:
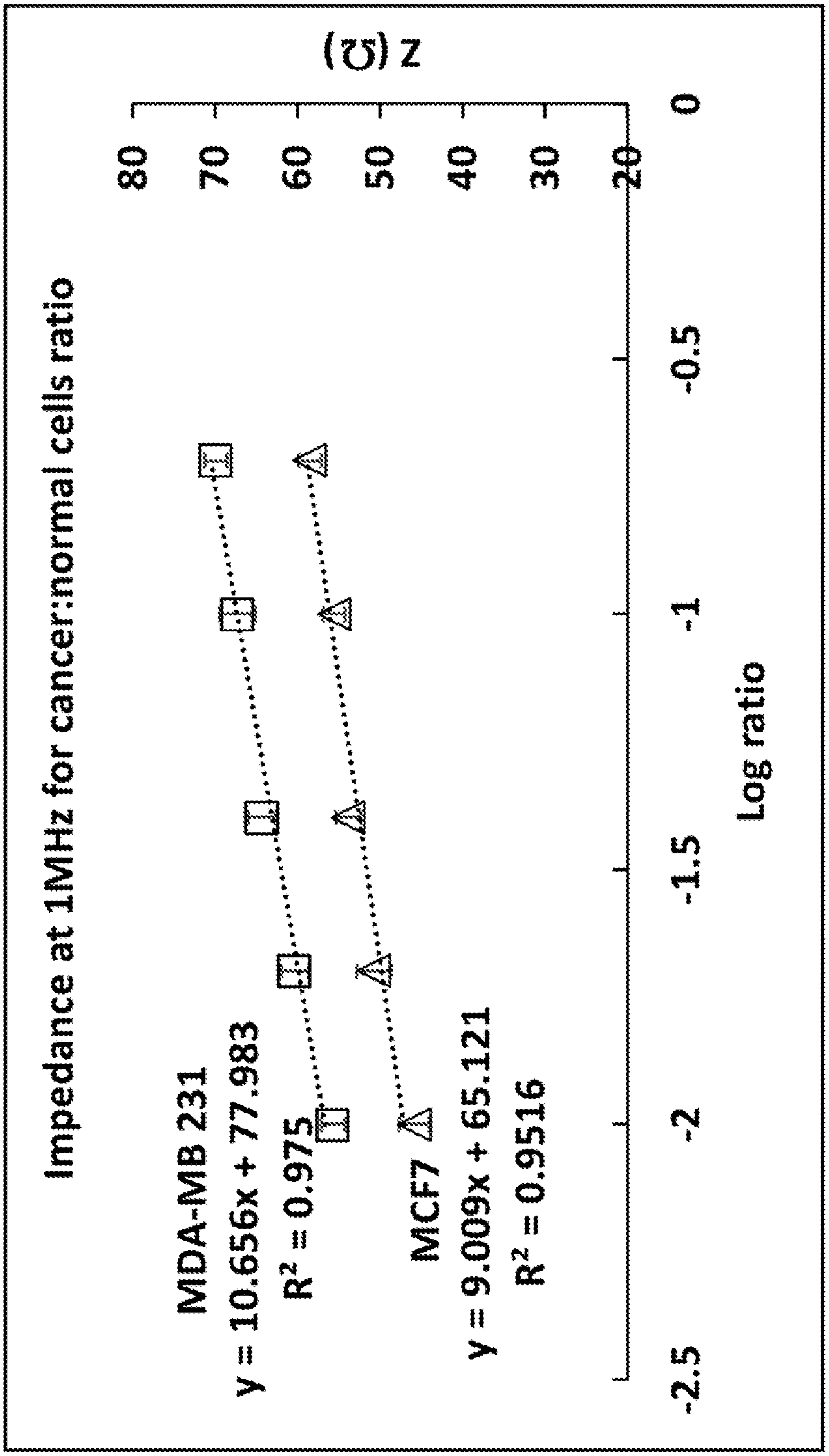
FIG. 20 shows impedance at 1 MHz for mixed samples, according to embodiments of the invention.

In this exemplary experiment, the MCF10A normal cells were mixed with the MCF7 and MDA 231 cancer cells, respectively, each across a wide range of mixing ratios, from 1:1,000 to 1:5 (FIG. 20). As shown in FIG. 20, a linear correlation between the lower mixing ratio and the higher corresponding impedance can help quantify how many cancer cells being mixed in the normal cells. This method, if combined with a simple cytofluorometry (for knowing the total number of cells), can be useful to detect the CTCs in a mixture with other cells, because other lab reported a 5% increase of the impedance from one cancer cell in 100 normal cells.

In literature, a study on these three cell-lines correlated a lower capacity with a higher malignance, due to the increase in the cell permeability for the pathologically more aggressive cancer cell. An electrophoresis study on the same three cell-lines showed significant differences in the cell membrane net-charge, showing cancer cells' more negative electric properties towards negativity more than observed in normal cells. These reports match our study, co-suggesting that our label-free nano-EIS sensor can distinguish normal from cancer cells, and differentiate the pathological malignance stages from early to late cancer progression.

Impedance Measurement for Warburg Effect on Breast Cancer and Colon Cancer Cell Lines: This test was done to investigate the effect of glucose on the cancer cell behaviors and in turn the impedance readings. The four cell-lines, e.g., MCF10A, MCF7, MDA-MB231, and HCT116, were suspended in an about 10 mL 1×PBS containing about 5.5 mM of glucose. The impedance measurement was done as described in the above. The parameters setup was by changing the frequency starting from about 40 kHz to about 1 MHz.

Figure 21:
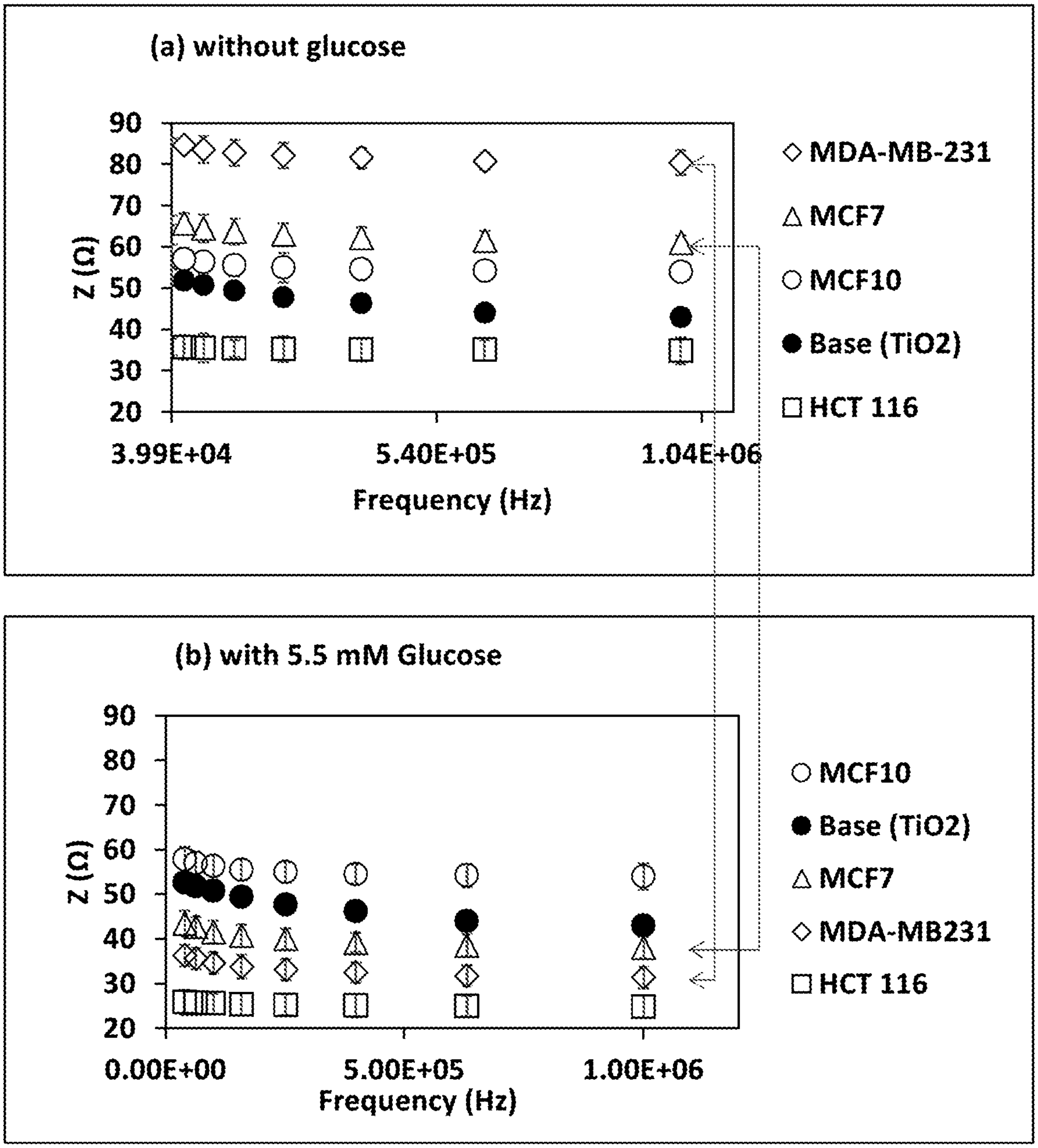
FIG. 21 shows impedance for different cancer cell lines with no glucose in 1×PBS (top panel) and impedance for cancer cells compared to normal cell incubated with 1×PBS+5.5 mM glucose (bottom panel), according to embodiments of the invention. P value for MCF7 and MDA 231 is less than $10^{-80}$.

The aim of this experiment is to quantify the effect of an electrically neutral metabolic fuel on the cancer cells, which is underexploited so far on an electrochemical nanosensor, but useful for quantifying and even characterizing cancer metabolic wastes, which is important in the basic cancer biology. As shown in FIG. 21, the cancer cells shifted their impedance level from above to below the base line differently from the normal cells, indicating that the normal and cancer cells secret different metabolic wastes each in a unique charge density to affect the nanowire-surface charge uniquely.

Cancer cells consume glucose and secrete lactic acid as a metabolic waste (i.e., Warburg effect), with a consistent upregulation of genes for the glucose transport and glycolysis, and the glucose transporters overexpress in hepatocarcinomas as well. By consuming more glucose than individual cancer cells, a tumor secretes a massive amount of lactate aiming to toxify the nearby normal cells more intensively, which can potentially result in a much stronger impedance signal on our bioscaffold sensor.

In cancer biology, under the help of overexpressed GLUT-1 that is activated by the HIF-1 protein, cancer cells tend to have a higher intake of glucose results in more production and secretion of the negative-charged lactic acids. Thus-increased $[H^+]$ on the nearby nanowire surface and increased in the nanowire-surface conductivity and lowered the impedance level, which is supported by the pH study shown in FIG. 10. The MCF7 and MDA 231 cancer cells each showed a significant shifting (FIG. 10) in their impedance level (see the red and blue arrows) after allowing the cells to intake the glucose, thus-proving the Warburg effect for quantifying and characterizing the cancer and normal cells directly on our smart bioscaffold-turned nano-biosensor.

In general, different types of cancer cells may secret different metabolic wastes as the biomarkers. For example, the HCT116 cells metabolism from an increase in the β-oxidation and urea cycle metabolism secrets four main metabolic wastes: N-acetylputrescine, phenylacetylglycine, deoxycarnitine or gamma-butyrobetaine (GBB) and butyrylcarnitine. These four metabolites each has an amide group in the structure. This explains why HCT116 act differently from other breast cancer cells on the titanate nanowire-bioscaffold. Overall, different cancer cells secrete different metabolite wastes as the cell's biomarker that if showing a charge in water can help quantify and characterize the cells on the titanate-nanowire bioscaffold-nanosensor.

Impedance Measurement for Temperature Effect on Breast Cancer Cell Lines at 37° C.: This test was conducted to determine if the temperature affect the different cell impedance. The cancer cell lines and the biosensor ($TiO_2$) where incubated for about 35 minutes. Impedance measurement was done as described previously under two different temperature, about 25° C. and about 37° C. The parameters setup was by changing the frequency starting from about 30 kHz to about 1 MHz.

Figure 22:
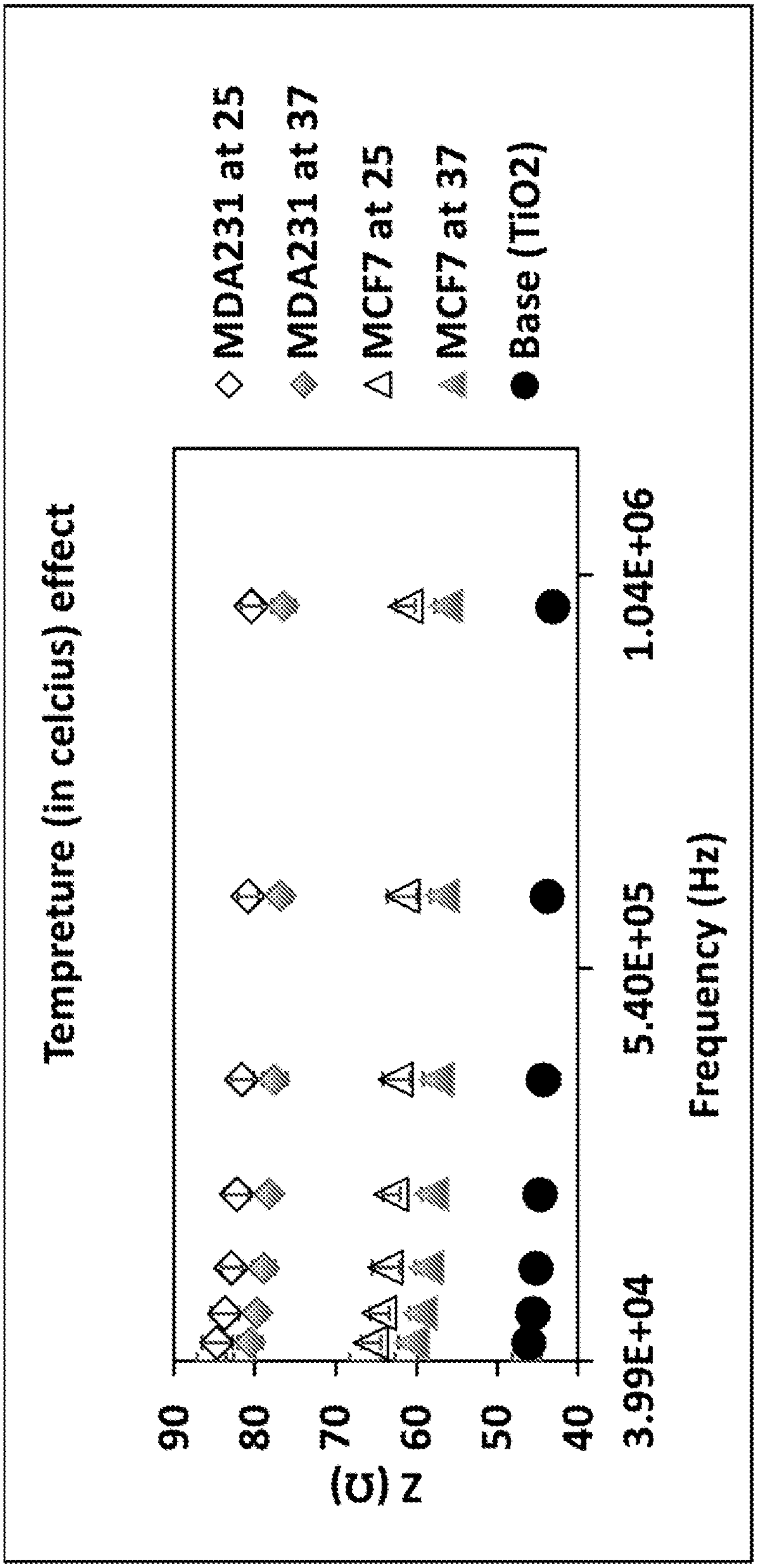
FIG. 22 shows impedance level of MCF7 and MDA 231 at 37° C., according to embodiments of the invention.

The abovementioned impedance measurements done at room temperature (25° C.) have raised a question regarding whether, and if yes how, the temperature that affects the cancer cell metabolism would change the impedance level at human body temperature 37° C. In this example, the MCF7 and MDA 231 cells were attached on the bio scaffold, respectively, over 35 minutes at a temperature of 37° C., and the impedance tests were done at the same temperature. The impedance level for MCF7 and MDA 231 breast cell lines show no significant shifting in impedance signal intensity, as shown in FIG. 22.

Figure 23:
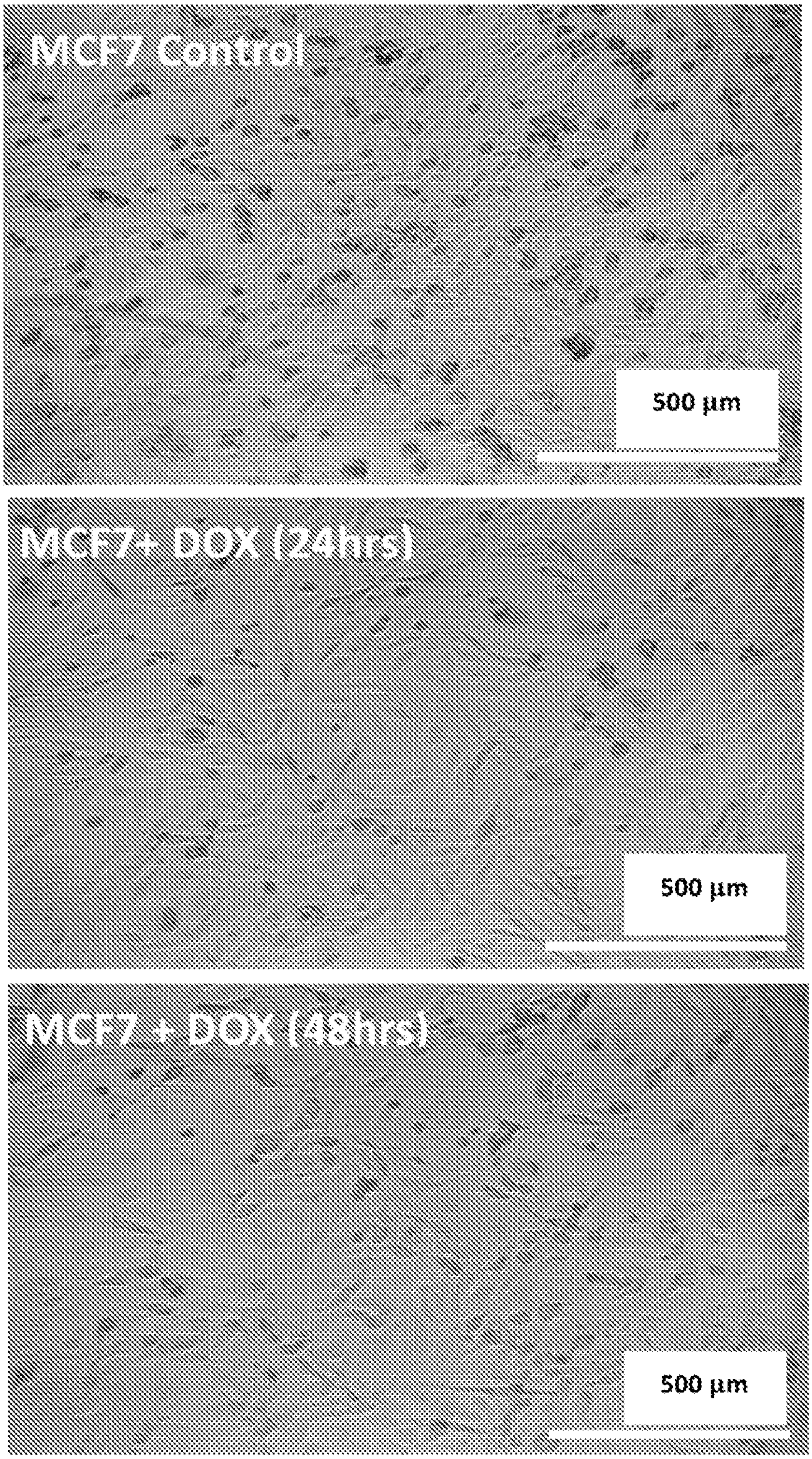
FIG. 23 shows microscopic images to drug treated MCF7 in cell culture compared to control, according to embodiments of the invention.

Impedance Measurement for Doxorubicin Drug Effect on Breast Cancer Cell Lines: This test was performed to investigate the effect of a well-known chemotherapy drug Doxorubicin on two different cancer cell lines. Doxorubicin (DOX, $C_{27}H_{29}NO_{11}$), also called Adriamycin™, is a popular chemotherapy drug for treating several types of cancer including breast cancer via triggering the cancer cell death. This drug was used to quantify the drug effect on breast cancer cells' metabolism in response to stresses from different dosages of the DOX, via monitoring the impedance signal change from the cancer cells before and after the DOX treatment. The drug cytotoxicity was assessed to determine the concentration of 2.0 μM, which the cancer cells start to die in a proper pace that can enable us to quantitatively characterize the DOX effect on the cancer cell's metabolism and apoptosis directly on the smart bioscaffold, as shown in FIG. 23.

MCF7 is known to be more resistive to DOX than MDA-MB231. To investigate the cell impedance change due to the DOX, the two cell lines were first cultured to reach about 90% confluence and then the DOX (2 μM) was added over two time-intervals, about 24 hours and about 48 hours. The cells were then harvested using trypsin and counted using the hemocytometer and trypan blue stain to control the cell number. The cells were then suspended in about 10 mL of 1×PBS with the $TiO_2$ nanowires sensor for about 35 minutes, and the impedance was tested likewise from about 40 kHz to about 1 MHz. The DOX is supposed to decrease the MCF7 impedance due to cell's resistance to the DOX. This is because the overexpressed P-glycoprotein 1 (P-gp), also called multidrug resistance protein 1 (MDR1) or ATP-binding cassette sub-family B member 1 (ABCB1) or cluster of differentiation 243 (CD243), can pump the foreign molecules out of the MCF7 cell.

Figure 24:
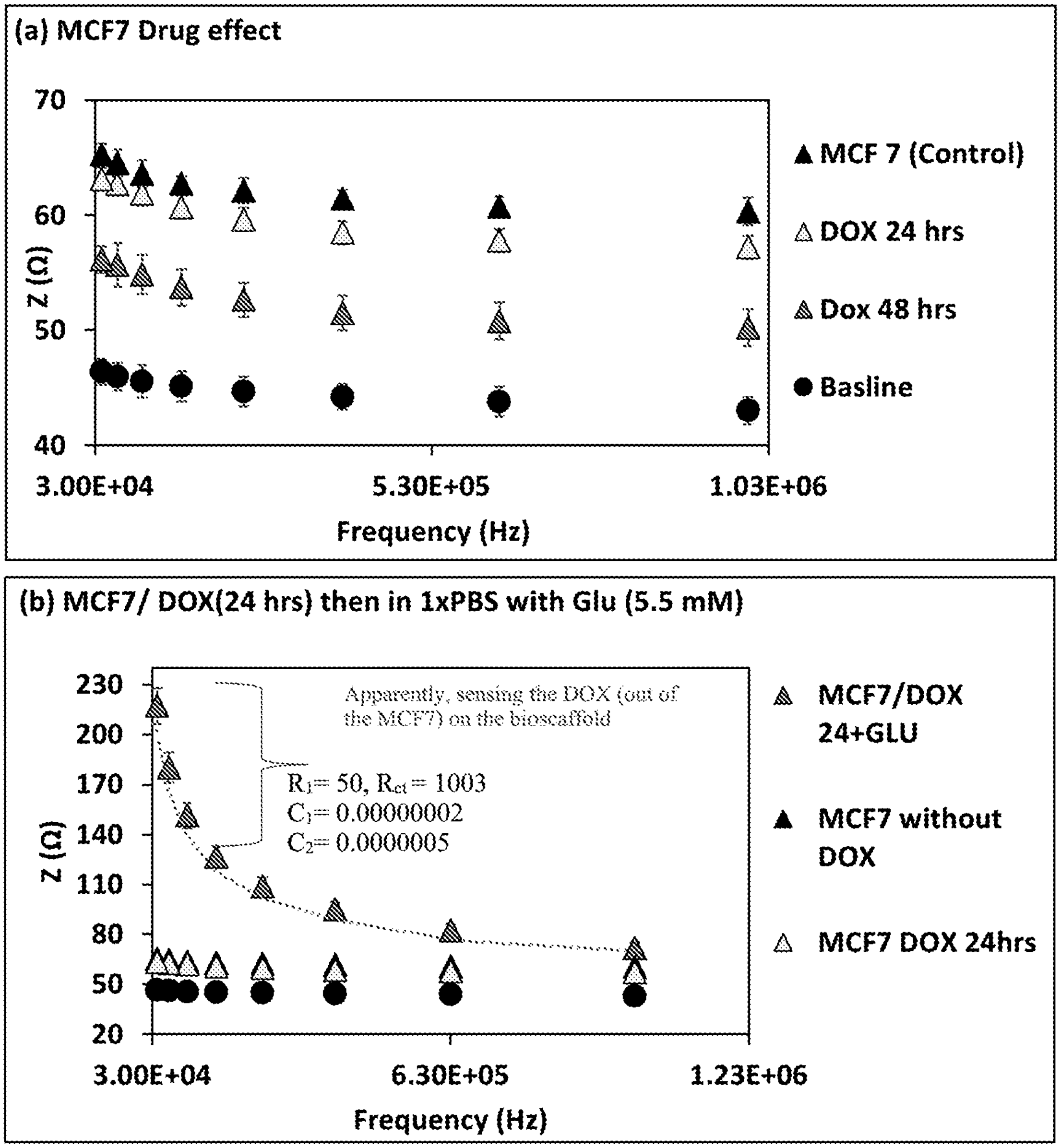
FIG. 24 shows (a) impedance for MCF7 treated with DOX for 24 and 48 hrs (top panel) and impedance for MCF7 treated with DOX for 24 hrs and then incubated with glucose for 35 minutes before performing the measurement (bottom panel), according to embodiments of the invention.
Figure 25:
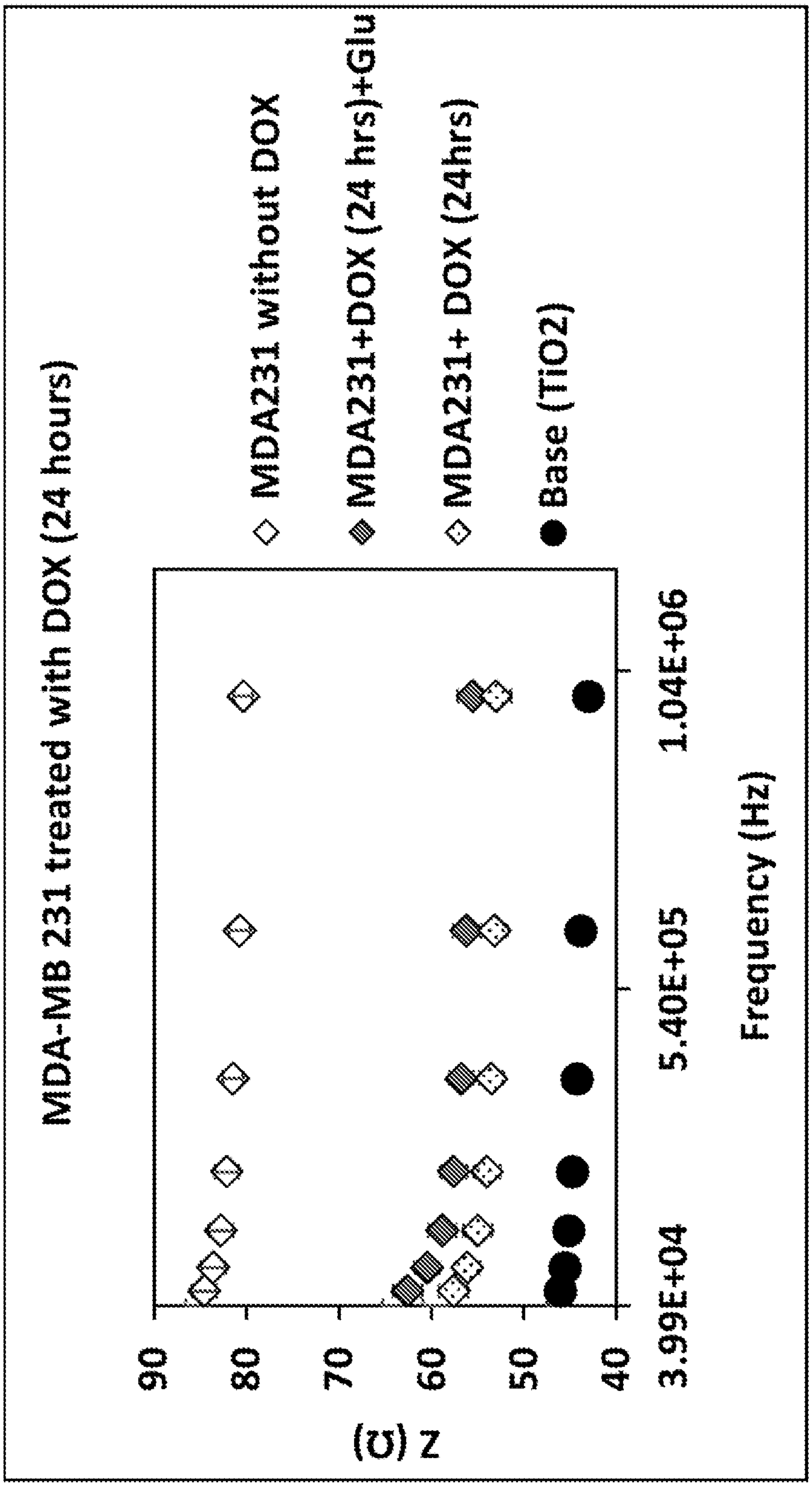
FIG. 25 shows impedance of MDA-MB231 treated with DOX for 24 hrs and being incubated with glucose before the measurement, according to embodiments of the invention.

The second set of experiment was done as in the first step, with glucose (5.5 mM) in the cell suspensions to investigate the cell impedance correspondence to glucose effect after being treated with DOX. The biosensors were done after about 35 minutes in the cell suspension, with the impedance parameters same as described previously. Due to MCF7 cell's resistance to DOX, incubating MCF7 with glucose helped MCF7 cell to flush the pre-absorbed DOX out to the extracellular solution, which should result in a higher impedance on the bioscaffold at low frequency due to the DOX negative in charge at physiological pH 7.4, as shown in FIG. 24. In contrast, the MDA 231 cells, with a much lower resistance to DOX, should show a lower impedance under the same condition, and no significant response to glucose after being pre-treated with DOX, as shown in FIG. 25.

Microscopic Visualization Using Fluoresce Staining

Figure 26:
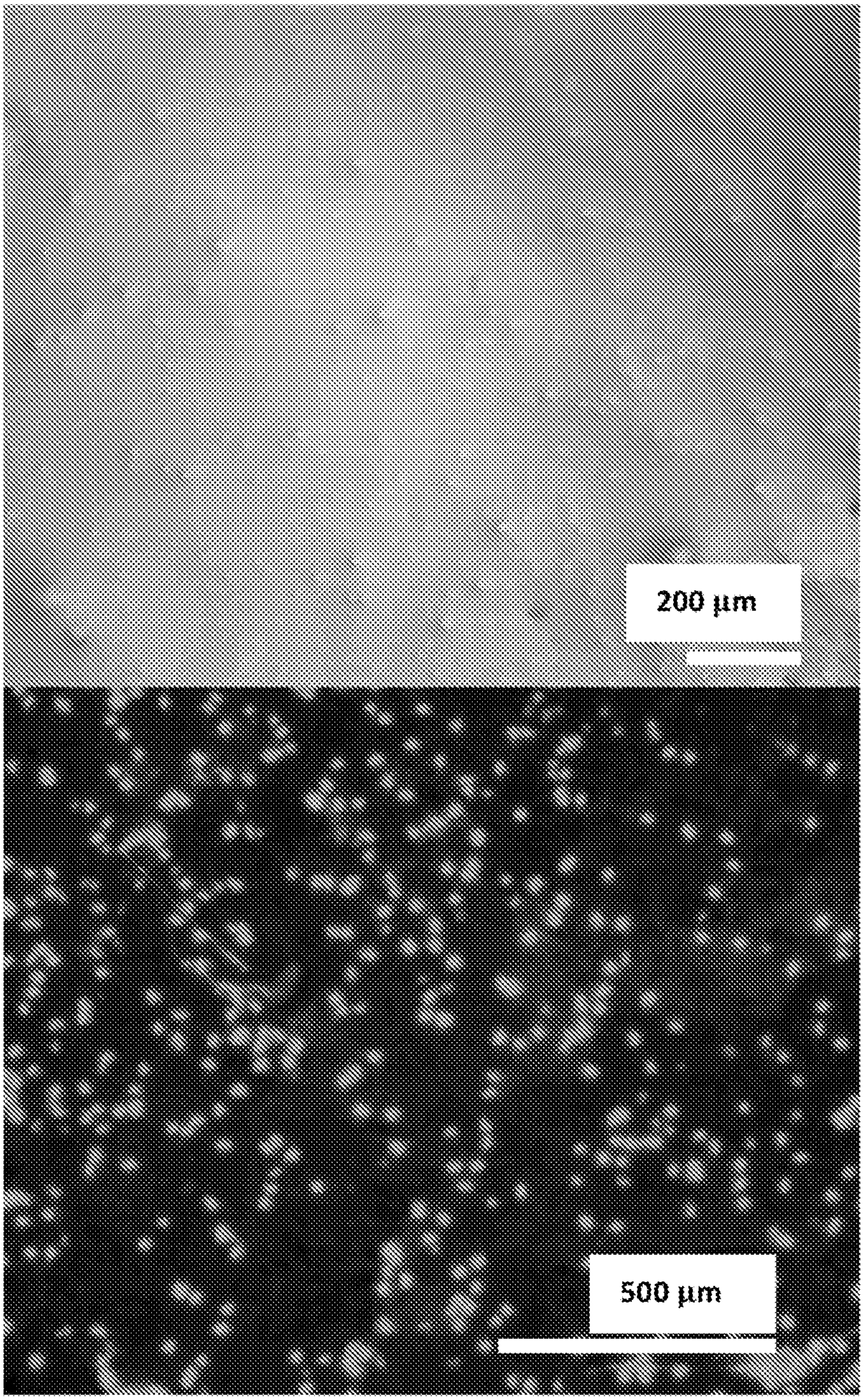
FIG. 26 shows optical microscopic images of the cells on bio scaffold without stain (top panel) and with fluorescent stain (bottom panel), according to embodiments of the invention.

After the data collection, the three scaffolds were dyed with SYTO®24 Green-Fluorescent Nucleic Acid stain (from Life Technology) with 490 absorptions and 515 emission wavelengths to visualize the attached cells. After fluorescence images were taken by Olympus BX41 microscope, cells were detached with trypsin and washed until no significant fluorescence could be seen. The measurement confirms the attachment of cells to the $TiO_2$ nanowire surface and confirming that the change in nanowire resistivity is coming from cell attachment, as shown in FIG. 26.

Before and after the measurements of the impedance, the normal and cancerous cells on the bioscaffolds were evaluated under the optical microscope. The cells population changes on the bioscaffolds were negligible, which supports why the impedance cell-sensing was kept within the 35 minutes.

Figure 27:
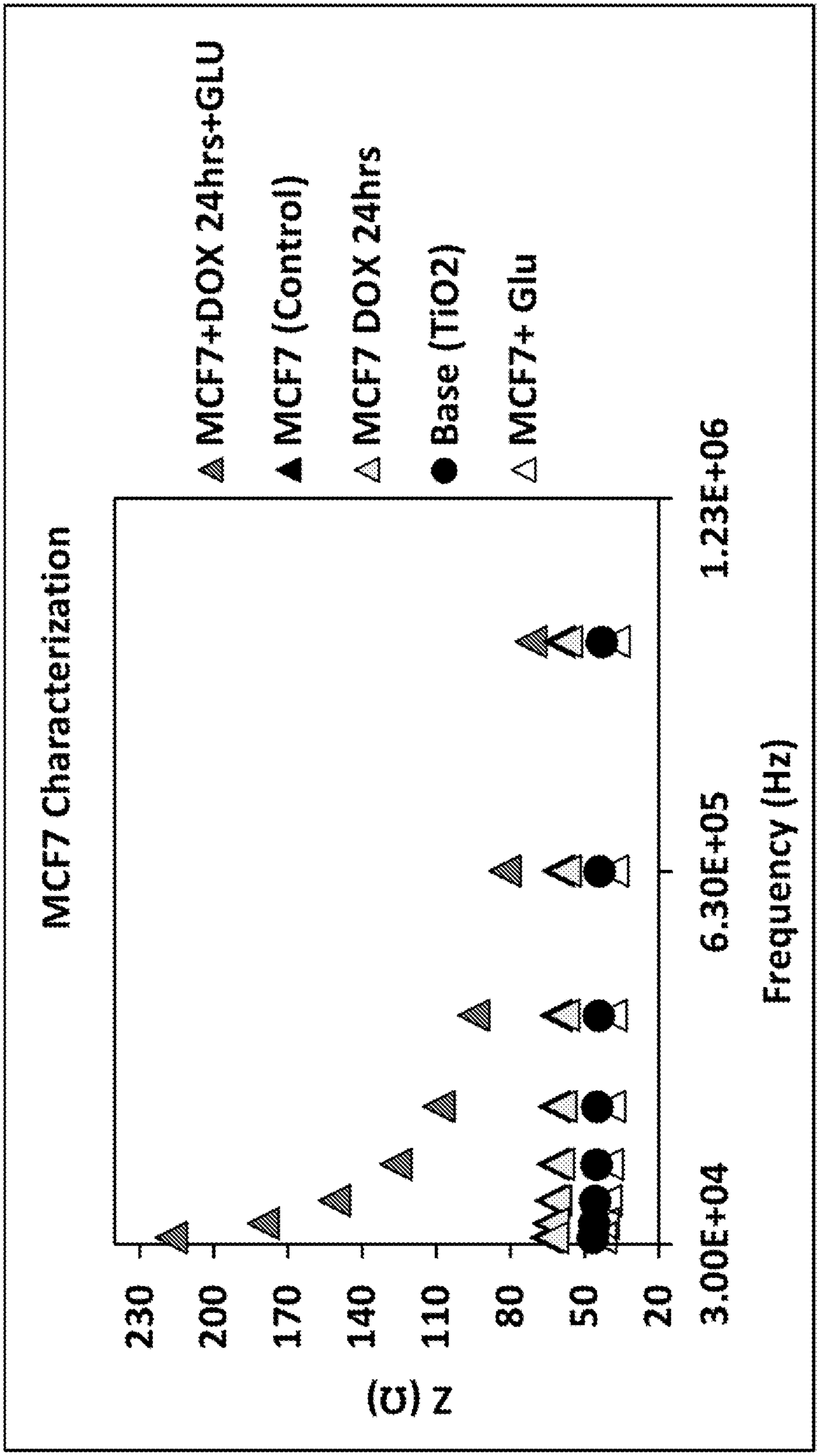
FIG. 27 shows MCF7 characterization according to embodiments of the invention.
Figure 28:
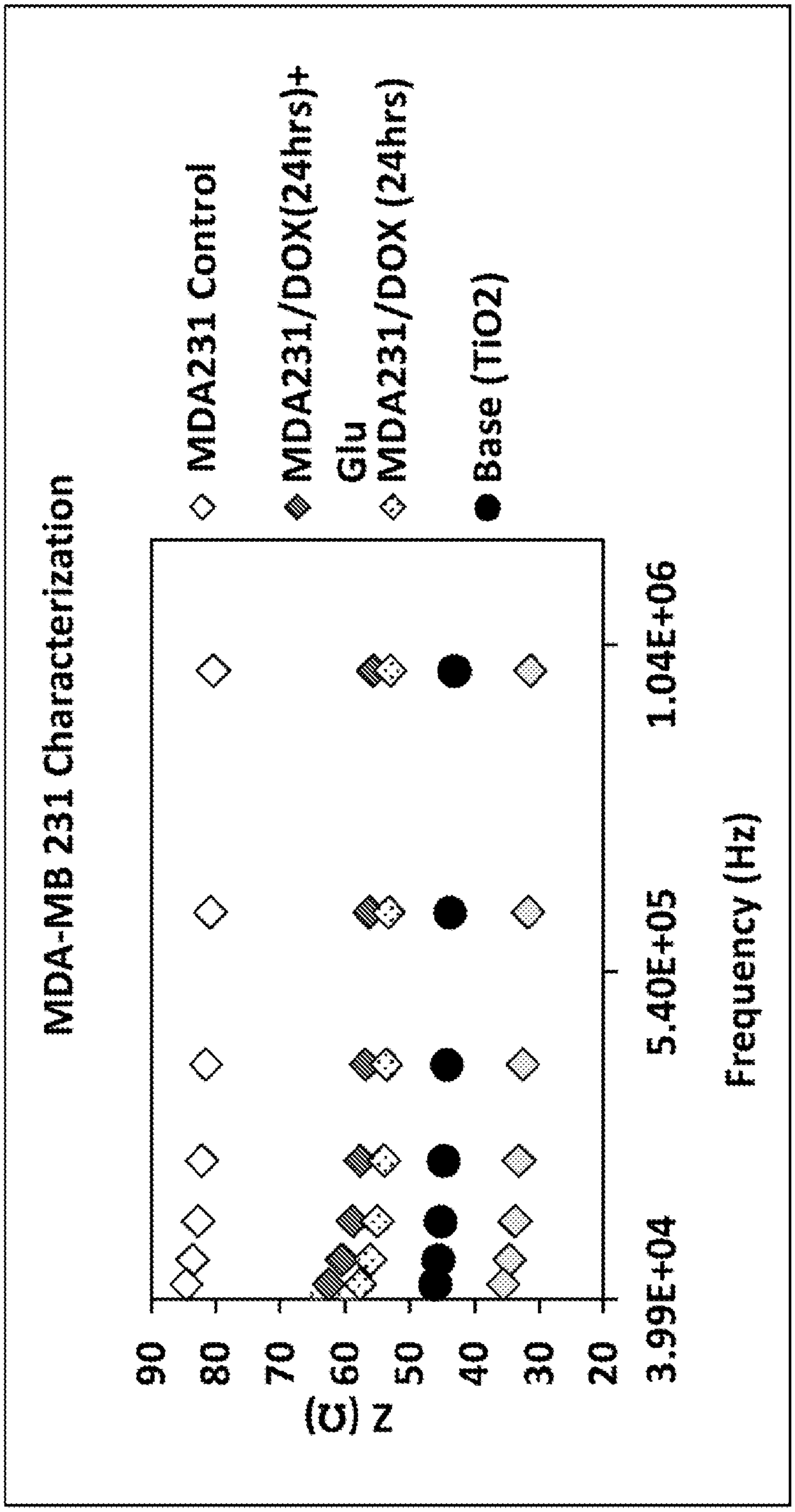
FIG. 28 shows MDA-MB231 characterization according to embodiments of the invention.

Briefly, according to the invention, the bioscaffold sensor can differentiate the pathological stage for the benign and malignant cancer cells. Different cancer cells from different origins (e.g., colon cancer vs. breast cancer) show different impedance responses upon binding and metabolizing to the nanowire surface, which can be utilized for advancing the cancer biology. Mixing cancer cells with normal cells over a wide range has further validated the novel cell-sensing technology. Quantifying the cancer drug's efficacy is investigated. The sensing for the glucose effect shows a partial reversibility of the cancer-drug effect different for different types of the cancer cells. On this basis, the characteristic fingerprints of cancer cells have been concluded in FIG. 27 for MCF7 cells, and in FIG. 28 for the MDA-MB231, which may change the game in today's cancer-pathology labs, via thus-sensing other cells on the smart-bioscaffolds.

The $TiO_2$ nanowire based cell-sensors according to embodiments of the invention are simple, sensitive, reliable, quick and direct (no labeling) in sensing, long shelf-life, adaptable to pathological lab setting. In addition, the sensors are easily to be fabricated in a large scale at low-cost.

In addition, the novel cell-sensing technology can be generalized to all kinds of charge species besides the biological cells, as well, tissues, bacteria, virus, eggs, and live insects.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various non-patent literature publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1]. Hanan, A.; Du, Y.; Zhou, J.; Tian, Z. R.; A Cell-Sensory Bioscaffold of Biocompatible Titanate Nanofiber, Proceedings of the 2018 *TechConnect World Innovation Conference*, Anaheim, LA, (To be published on May 13-16, 2018).

[2]. Wang, R. H.; Dong, W. J.; Ruan, C. M.; Kanayeva, D.; Lessiter, K.; Tian, Ryan; Li, Y. B.; TiO2 Nanowire Bundle Microelectrode Based Impedance Immunosensor for Rapid and Sensitive Detection of *Listeria monocytogenes, Nano Lett.,* 9 (12), 45704570 (2008).

[3]. Dong, W.; Zhang, T.; Epstein, J.; Cooney, L.; Wang, H.; Li, Y.; Jiang, Y-B.; Cogbill, A.; Tian, Z. Ryan; Multifunctional Nanowire Bioscaffolds on Titanium, *Chem. Mater,* 19, 4454-4459 (2007).

[4]. Dong, W. Zhang, T.; McDonald, M.; Padilla, C.; Epstein, J.; Tian, Z. R.; "Biocompatible nanofiber scaffolds on metal for controlled release and cell colonization," Nanomedicine: Nanotech., *Biology*, & *Medicine,* 2, 248-252 (2006).

[5]. Abraham, J. K.; Dubaka, S.; Varadan, V. K.; Zhou, H.; Zhang, T.; Tian, Z. Ryan; Piezoelectric 3D nanostructures for developing point-of-care biosensors, SPIE Proc, 6528, 04-11-2007. Asphahani, F. et al. Influence of cell adhesion and spreading on impedance characteristics of cell-based sensors. *Biosensors & Bioelectronics* 23, 1307-1313, doi: 10.1016/j.bios.2007.11.021 (2008).

[6]. Asphahani, F. et al. Single-cell bioelectrical impedance platform for monitoring cellular response to drug treatment. *Physical Biology* 8, doi:10.1088/1478-3975/8/1/015006 (2011).

[7]. Blad, B. & Baldetorp, B. Impedance spectra of tumour tissue in comparison with normal tissue; A possible clinical application for electrical impedance tomography. *Physiological Measurement* 17, A105-A115, doi:10.1088/0967-3334/17/4a1015 (1996).

[8]. Cho, Y., Kim, H S., Frazier, A B., Chen, Z G., Shin, D M. & Han, A. Whole-cell impedance analysis for highly and poorly metastatic cancer cells. *Journal of Microelectromechanical Systems* 18(4), 808-817 (2009).

[9]. Cui, Y., An, Y., Jin, T Y., Zhang, F. & He, P G. Real-time monitoring of skin wound healing on nano-grooves topography using electric cell-substrate impedance sensing (ECIS). *Sensors and Actuators B-Chemical* 250, 461-468 (2017).

[10]. Dean, D. A., Ramanathan, T., Machado, D. & Sundararajan, R. Electrical impedance spectroscopy study of biological tissues. *Journal of Electrostatics* 66, 165-177, doi:10.1016/j.elstat.2007.11.005 (2008).

[11]. Dobrzynska, I., Skrzydlewska, E. & Figaszewski, Z. A. Changes in Electric Properties of Human Breast Cancer Cells. *Journal of Membrane Biology* 246, 161-166, doi: 10.1007/s00232-012-9516-5 (2013).

[12]. Dong, W.; Zhang, T.; Epstein, J.; Cooney, L.; Wang, H.; Li, Y.; Jiang, Y-B.; Cogbill, A.; Tian, Z. Ryan; Multifunctional Nanowire Bioscaffolds on Titanium, *Chem. Mater,* 19, 4454-4459, 2007.

[13]. Dong, W. Zhang, T.; McDonald, M.; Padilla, C.; Epstein, J.; Tian, Z. R.; "Biocompatible nanofiber scaffolds on metal for controlled release and cell colonization," *Nanomedicine: Nanotech., Biology, & Medicine,* 2006, 2, 248252.

[14]. Foster, K. R. & Schepps, J. L. DIELECTRIC-PROPERTIES OF TUMOR AND NORMAL-TISSUES AT RADIO THROUGH MICROWAVE-FREQUENCIES. *Journal of Microwave Power and Electromagnetic Energy* 16, 107-119 (1981).

[15]. Foster, K. R. & Schwan, H. P. DIELECTRIC-PROPERTIES OF TISSUES AND BIOLOGICAL-MATERIALS—A CRITICAL-REVIEW. *Critical Reviews in Biomedical Engineering* 17, 25-104 (1989).

[16]. Ghenim, L. et al. Monitoring impedance changes associated with motility and mitosis of a single cell. *Lab on a Chip* 10, 2546-2550, doi:10.1039/c004115g (2010).

[17]. Giaever, I. & Keese, C. R. MICROMOTION OF MAMMALIAN-CELLS MEASURED ELECTRICALLY. *Proceedings of the National Academy of Sciences of the United States of America* 88, 7896-7900, doi:10.1073/pnas.88.17.7896 (1991).

[18]. Giaever, I. & Keese, C. R. MONITORING FIBROBLAST BEHAVIOR IN TISSUE-CULTURE WITH AN APPLIED ELECTRIC-FIELD. *Proceedings of the*

*National Academy of Sciences of the United States of America-Biological Sciences* 81, 3761-3764, doi: 10.1073/pnas.81.12.3761 (1984).

[19]. Glickman, Y. A. et al. Electrical impedance scanning: a new approach to skin cancer diagnosis. *Skin Research and Technology* 9, 262-268, doi:10.1034/j.1600-0846.2003.00022.x (2003).

[20]. Goller, D. A., Weidema, W. F. & Davies, R. J. TRANSMURAL ELECTRICAL POTENTIAL DIFFERENCE AS AN EARLY MARKER IN COLON CANCER. *Archives of Surgery* 121, 345-350 (1986).

[21]. Han, A., Yang, L. & Frazier, A. B. Quantification of the heterogeneity in breast cancer cell lines using whole-cell impedance spectroscopy. *Clinical Cancer Research* 13, 139-143, doi:10.1158/1078-0432.ccr-06-1346 (2007).

[22]. Hanan, A.; Du, Y.; Zhou, J.; Tian, Z. R.; A Cell-Sensory Bioscaffold of Biocompatible Titanate Nanofiber, Proceedings of the 2018 TechConnect World Innovation Conference, Anaheim, LA, (To be published on May 13-16, 2018). Holder & David. *Electrical impedance tomography: methods, history, and applications.* 488 (Institute of Physics Pub, 2005).

[23]. Jossinet, J. The impedivity of freshly excised human breast tissue. *Physiological Measurement* 19, 61-75, doi: 10.1088/0967-3334/19/1/006 (1998).

[24]. Jossinet, J. Variability of impedivity in normal and pathological breast tissue. *Medical & Biological Engineering & Computing* 34, 346-350, doi:10.1007/bf02520002 (1996).

[25]. Mitra, P., Keese, C. R. & Giaever, I. Electric measurements can be used to monitor the attachment and spreading of cells in tissue-culture. *Biotechniques* 11, 504-& (1991).

[26]. Morimoto, T. et al. MEASUREMENT OF THE ELECTRICAL BIOIMPEDANCE OF BREAST-TUMORS. *European Surgical Research* 22, 86-92, doi:10.1159/000129087 (1990).

[27]. O'Rourke, A. P. et al. Dielectric properties of human normal, malignant and cirrhotic liver tissue: in vivo and ex vivo measurements from 0.5 to 20 GHz using a precision open-ended coaxial probe. *Physics in Medicine and Biology* 52, 4707-4719, doi:10.1088/0031-9155/52/15/022 (2007).

[28]. Pethig, R. Dielectric properties of body tissues. *Clinical physics and physiological measurement: an official journal of the Hospital Physicists' Association, Deutsche Gesellschaft fur Medizinische Physik and the European Federation of Organisations for Medical Physics* 8 Suppl A, 5-12, doi:10.1088/0143-0815/8/4a1002 (1987).

[29]. Pethig, R. DIELECTRIC-PROPERTIES OF BIOLOGICAL-MATERIALS—BIOPHYSICAL AND MEDICAL APPLICATIONS. *IEEE Transactions on Electrical Insulation* 19, 453-474, doi:10.1109/tei.1984.298769 (1984).

[30]. Polk, C. & Postow, E. CRC handbook of biological effects of electromagnetic fields. *CRC handbook of biological effects of electromagnetic fields.*, i-xiii, 1-503 (1986).

[31]. Qiao, G. F. et al. Bioimpedance Analysis for the Characterization of Breast Cancer Cells in Suspension. *IEEE Transactions on Biomedical Engineering* 59, 2321-2329, doi:10.1109/tbme.2012.2202904 (2012).

[32]. Richard J & Davies. *Underlying mechanisms involved in surface electrical potential measurements for the diagnosis of breast cancer an electrophysiological approach to cancer diagnosis, In Electropotentials in the Clinical Assessment of Breast Neoplasia.* pp 3-17 (1996).

[33]. Schwan, H. P. Electrical properties of tissue and cell suspensions. *Advances in biological and medical physics* 5, 147-209 (1957).

[34]. Srinivasaraghavan, V., Strobl, J. & Agah, M. Bioimpedance rise in response to histone deacetylase inhibitor is a marker of mammary cancer cells within a mixed culture of normal breast cells. *Lab on a Chip* 12, 5168-5179, doi:10.1039/c21c40778g (2012).

[35]. Vistejnova, L. et al. The comparison of impedance-based method of cell proliferation monitoring with commonly used metabolic-based techniques. *Neuroendocrinology Letters* 30, 121-127 (2009).

[36]. Wang, R. H.; Dong, W. J.; Ruan, C. M.; Kanayeva, D.; Lessiter, K.; Tian, Ryan; Li, Y. B.; TiO2 Nanowire Bundle Microelectrode Based Impedance Immunosensor for Rapid and Sensitive Detection of *Listeria monocytogenes, Nano Lett.,* 9 (12), 4570-4570, 2008.

[37]. Wanekaya, A. K., Chen, W., Myung, N. V. & Mulchandani, A. Nanowire-based electrochemical biosensors. *Electroanalysis* 18, 533-550, doi:10.1002/elan.200503449 (2006).

[38]. Wegener, J., Keese, C. R. & Giaever, I. Electric cell-substrate impedance sensing (ECIS) as a noninvasive means to monitor the kinetics of cell spreading to artificial surfaces. *Experimental Cell Research* 259, 158-166, doi: 10.1006/excr.2000.4919 (2000).

[39]. Xiao, C. & Luong, J. H. T. On-line monitoring of cell growth and cytotoxicity using electric cell-substrate impedance sensing (ECIS). *Biotechnology Progress* 19, 1000-1005, doi:10.1021/bp025733x (2003).

[40]. Yang, L. J., Arias, L. R., Lane, T. S., Yancey, M. D. & Mamouni, J. Real-time electrical impedance-based measurement to distinguish oral cancer cells and non-cancer oral epithelial cells. *Analytical and Bioanalytical Chemistry* 399, 1823-1833, doi:10.1007/s00216-010-4584-9 (2011).

What is claimed is:

1. A cell sensor, comprising:

a sensing member having bioscaffolds comprising nanofibers/nanowires of titanate hydrothermally grown directly on a titanium sheet, wherein the nanofibers/nanowires of titanate are entangled atop and self-assembled during the hydrothermal growth into scaffolds comprising concave nests formed by the entangled nanowires, wherein the concave nests form cell-scale trapping structures configured to localize live cells within the concave nests and to modulate surface charge density upon cell binding; wherein the entangled nanowires within the concave nests define a circular arrangement configured to provide nanowire induction; wherein the bioscaffolds comprise a surface chemistry of H (Na)-titanate having a point of zero charge (PZC) of about pH 7; and an electrode coupled to the titanium sheet to form an electrochemical sensing interface configured to apply an alternative current (AC) excitation signal;

wherein the circular arrangement of the entangled nanowires within the concave nests generates an inductive electromagnetic field in response to the AC excitation signal, and wherein an impedance response of the cell sensor is dependent on changes in surface charge density of the bioscaffolds upon cell binding.

2. The cell sensor of claim 1, wherein the nanofibers/nanowires of titanate are grown under a hydrothermal process at a predetermined temperature for a period of treating time.

3. The cell sensor of claim 2, wherein the predetermined temperature is in a range of about 128-300° C., and the period of treating time is in a range of about 3.2-30 hrs.

4. The cell sensor of claim 1, wherein the cells in the aqueous solution include at least one of cancer cells, normal cells, stem cells, and neuron cells, and different types of cells produce differences in impedance change within certain frequencies on the bioscaffolds.

5. The cell sensor of claim 4, wherein different ratios of the cancer cells in the normal cells shifted mixture's electrochemical signals quantitatively and reproducibly.

6. The cell sensor of claim 4, wherein the cancer cells alter the surface charge-density of the bioscaffolds more than that of the normal cells while binding to the surface of nanofibers/nanowires of the bioscaffolds.

* * * * *